(12) United States Patent
Yonehara et al.

(10) Patent No.: US 8,273,577 B2
(45) Date of Patent: Sep. 25, 2012

(54) METHOD FOR DETECTING PHENOTHIAZINE-DERIVATIVE COLOR AND COLOR-DEVELOPER REAGENT USED THEREIN

(75) Inventors: Satoshi Yonehara, Kyoto (JP); Norio Inamura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 416 days.

(21) Appl. No.: 12/524,834

(22) PCT Filed: Jan. 30, 2008

(86) PCT No.: PCT/JP2008/051388
§ 371 (c)(1),
(2), (4) Date: Jul. 28, 2009

(87) PCT Pub. No.: WO2008/093722
PCT Pub. Date: Aug. 7, 2008

(65) Prior Publication Data
US 2010/0112622 A1    May 6, 2010

(30) Foreign Application Priority Data
Jan. 30, 2007   (JP) .................................. 2007-020183

(51) Int. Cl.
*G01N 21/78* (2006.01)
(52) U.S. Cl. ........................................ 436/92; 436/164
(58) Field of Classification Search .................... 436/92, 436/93, 96, 164, 166, 174, 177
See application file for complete search history.

(56) References Cited

U.S. PATENT DOCUMENTS

| | | | | |
|---|---|---|---|---|
| 4,384,042 | A | | 5/1983 | Miike et al. |
| 4,916,058 | A | | 4/1990 | Aoyama et al. |
| 5,523,214 | A | * | 6/1996 | Horn ............................... 435/52 |
| 6,703,245 | B2 | | 3/2004 | Sumitani et al. |
| 2003/0082823 | A1 | | 5/2003 | Sumitani et al. |
| 2003/0157719 | A1 | | 8/2003 | Samsoondar |
| 2009/0053823 | A1 | | 2/2009 | Yonehara et al. |

FOREIGN PATENT DOCUMENTS

| | | |
|---|---|---|
| CN | 1448782 | 10/2003 |
| EP | 1788081 A1 | 5/2007 |
| EP | 1985670 A1 | 10/2008 |
| EP | 2108952 A1 | 10/2009 |
| GB | 1475876 | 6/1977 |
| JP | 60-33479 | 8/1985 |
| JP | 1-118768 | 5/1989 |
| JP | 4-27839 | 5/1992 |
| JP | 7-234221 | 9/1995 |
| JP | 7-289253 | 11/1995 |
| JP | 8-154672 | 6/1996 |
| JP | 8-336386 | 12/1996 |
| JP | 2000-214152 | 8/2000 |
| JP | 2000-214155 | 8/2000 |
| JP | 2000-300294 | 10/2000 |
| JP | 2002-315600 | 10/2002 |
| JP | 2004-045365 | 2/2004 |
| JP | 2004-275013 | 10/2004 |
| JP | 2004-275063 | 10/2004 |
| JP | 2004-344052 | 12/2004 |
| WO | 97/20039 | 6/1997 |
| WO | 00/50579 | 8/2000 |
| WO | 00/61732 | 10/2000 |
| WO | 02/06519 | 1/2002 |
| WO | 02/21142 | 3/2002 |
| WO | 2004/029251 | 4/2004 |
| WO | 2007/083703 | 7/2007 |
| WO | 2009/069309 A1 | 6/2009 |

OTHER PUBLICATIONS

Ducros, Veronique et al. "Methods for homocysteine analysis and biological relevance of the results." Journal of Chromatography B (2002) 781 207-226.*
Sakai, Yasuyoshi et al. "Purification and properties of fructosyl lysine oxidase from Fuasrium oxysporum S-1F4." Bioscience Biotechnology and Biochemistry (1995) 59 487-491.*
Sakaue, Ryoichi et al. "Thermostabilization of bacterial fructosyl-amino acid oxidase by directed evolution." Applied and Environmental Microbiology (2003) 69 139-145.*
Hamai, Sanyo. "Complex formation in cationic dye-organic anion systems in aqueous solution." Bull. Chem. Soc. Jpn. (1985) 58 2099-2106.*
Yamamoto, Shunzo et al. "Spectroscopic studies of the interaction between methylene blue—naphthol orange complex and anionic and cationic surfactants." Spectrochimica Acta Part A (Jul. 2006, online publication date) 66 302-306.*
Extended European Search Report issued in a related European Patent Application No. 08704155.4, dated Apr. 12, 2011.
Vytras, et al., "Achromatic screening of metallochromic indicators as a correction method for visual end-point location", Collection Czechoslov. Chem. Commun., 1976, vol. 41, pp. 2846-2856, particularly, Abstract and Fig. 3.
Specification, Claims, Abstract & Drawings from co-pending U.S. Appl. No. 12/933,569, filed Sep. 20, 2010—53 pages.
Extended European Search Report issued in corresponding European Patent Application No. 09722516.3 dated Mar. 8, 2012.

* cited by examiner

*Primary Examiner* — Vickie Kim
*Assistant Examiner* — Christopher A Hixson
(74) *Attorney, Agent, or Firm* — Morgan, Lewis & Bockius LLP

(57) ABSTRACT

The present invention provides a phenothiazine-derivative color-measuring method that can detect a phenothiazine-derivative color even at a wavelength longer than the wavelength that exhibits maximum absorption. A phenothiazine-derivative color is detected, by adding a 5-hydroxy-1-(4-sulfophenyl)-4-(4-sulfophenylazo)pyrazole-3-carboxylic acid salt, 6-hydroxy-5-(4-sulfophenylazo)-2-naphthalenesulfonic acid salt, 3-hydroxy-4-(4-sulfonaphthylazo)-2,7-naphthalenedisulfonic acid salt, 7-hydroxy-8-(4-sulfonaphthylazo)-1,3-naphthalenedisulfonic acid salt, 3',6'-dihydroxy-2',4',5',7'-tetraiodospiro[isobenzofuran-1(3H),9'-(9H)xanthene]-3-one salt, 3',6'-dihydroxy-2',4',5',7'-tetrabromo-4,5,6,7,-tetrachlorospiro[isobenzofuran-1(3H),9'-[9H]xanthene]-3-one salt, 4,5,6,7-tetrachloro-3',6'-dihydroxy-2',4',5',7'-tetraiodospiro[isobenzofuran-1(3H),9'-[9H]xanthene]-3-one salt or flavonoid-based color to the reaction system containing a phenothiazine-derivative color, and then measuring the light absorbance at a wavelength of 610 to 730 nm.

25 Claims, 4 Drawing Sheets

METHOD FOR DETECTING PHENOTHIAZINE-DERIVATIVE COLOR AND COLOR-DEVELOPER REAGENT USED THEREIN

TECHNICAL FIELD

The present invention relates to a method for detecting a phenothiazine-derivative color, a method for measuring a target component using detection of a phenothiazine-derivative color, and a color-developer reagent used therein.

BACKGROUND ART

As a method for performing measurement (qualitative or quantitative analysis) of a target component, an enzymic method using oxidation-reduction commonly is put in practice. According to this method, for example, an oxidizing substance is produced from a target component that is to be measured, this oxidizing substance and a color-developer that produces a color-developed compound through oxidation are caused to react by an oxidizing enzyme, and the light absorbance of the color development that occurs is measured. In this method, the light absorbance corresponds to the amount of color-developed compound produced, the amount of color-developed compound produced corresponds to the amount of oxidizing substance produced, and the amount of oxidizing substance corresponds to the amount of target component. That is to say, a target component can be measured indirectly through such oxidation-reduction, by detecting the color development that occurs (produced color-developed compound).

Examples of a color-developer used in the enzymic method include Trinder's reagent and N-(carboxymethylaminocarbonyl)-4,4'-bis(dimethylamino)diphenylamine sodium salt (product name DA-64; manufactured by Wako Pure Chemical Industries, Ltd.). Furthermore, known examples of a color-developer that produces a phenothiazine-derivative color, such as methylene blue, which is a color-developed compound, include 10-(carboxymethylaminocarbonyl)-3,7-bis(dimethylamino)phenothiazine salt (product name DA-67; manufactured by Wako Pure Chemical Industries, Ltd., hereinafter, also referred to as "DA-67"), 10-(acetylaminocarbonyl)-3,7-bis(dimethylamino)phenothiazine, 10-(phenylcarbonyl)-3,7-bis(dimethylamino)phenothiazine as described in Patent Document 3, 10-(3-(methylcarboxyamino)-hexamethyl-amino)-phenothiazine as described in Patent Document 4, 10-(3-(methylcarboxyamino)-4-methyl-phenyl)-amino)-phenothiazine, 10-((3-(methylcarboxyamino methyl)-phenyl)-methylamino)-phenothiazine, 10-(1-naphthaleneamino)-phenothiazine, 10-(methyl)-phenothiazine, 10-(phenylamino)-phenothiazine, 10-(methylamino)-phenothiazine, and the like. Phenothiazine-derivative color has a maximum absorption at 590 to 670 nm, which is on a relatively long-wavelength side, and, thus, among these, a color-developer such as DA-67 that produces a phenothiazine-derivative color such as methylene blue is considered to be important because of the following reasons.

That is to say, a sample such as a bodily fluid contains not only a target component but also various other components, and these components may have an absorption in a range with a wavelength of around 500 nm or shorter. Thus, in the above-described enzymic method, in order to avert the influence of components other than the target component, a color-developed compound produced through oxidation-reduction preferably can be detected at a wavelength that is as long as possible. Thus, a color-developer such as DA-67 that produces a phenothiazine-derivative color having a maximum absorption at 590 to 670 nm as described above is considered to be particularly useful.

However, for example, samples containing hemoglobin (hereinafter, referred to as "Hb"), such as a whole blood sample or a blood cell sample, may exhibit an absorption that can affect detection of a color at approximately 570 to 630 nm. Moreover, when Hb is methylated, the samples may exhibit an absorption that can affect detection of a phenothiazine-derivative color at approximately 570 to 670 nm. Accordingly, even with the above-described color-developer that produces a phenothiazine-derivative color, the measurement may be influenced in the case where the color-developer is applied to these sort of samples.

Moreover, there are clinical chemistry-specific automatic analyzing apparatuses in which the detection wavelength is fixed, for example, not to 610 to 660 nm but to 700 nm. However, a phenothiazine-derivative color having a maximum absorption at 610 to 670 nm is extremely difficult to detect at 700 nm, and, thus, the measurement cannot be performed with present analyzing apparatuses having a detection wavelength at 700 nm.

For example, blue-colored methylene blue is reduced to colorless leucomethylene blue. Using these characteristics, a target component can be measured also by a method in which a phenothiazine-derivative color itself such as methylene blue is used as the color-developer, the phenothiazine-derivative color is reduced with a reducing substance produced by the target component, and the disappearance of blue color through such reduction (decrease in the phenothiazine-derivative color) is measured (Patent Documents 1 and 2). However, also in this case, problems as described above occur.

[Patent Document 1] JP 2000-214152A
[Patent Document 2] JP 2000-214155A
[Patent Document 3] JP H4-27839B
[Patent Document 4] JP S60-33479B

DISCLOSURE OF INVENTION

It is an object of the present invention to provide a phenothiazine-derivative color-measuring method that can detect a phenothiazine-derivative color even at a wavelength longer than the wavelength that exhibits the maximum absorption.

A method for detecting a phenothiazine-derivative color of the present invention is a method for detecting a phenothiazine-derivative color in a reaction system by measuring a light absorbance, comprising a step of detecting a phenothiazine-derivative color, wherein, in the detecting step, a phenothiazine-derivative color is detected in the presence of at least one color substance selected from the group consisting of a compound represented by Formula (I) below, a compound represented by Formula (II) below, and a flavonoid-based color:

$$R^1-N=N-R^2 \quad (I)$$

(in Formula (I), $R^1$ is

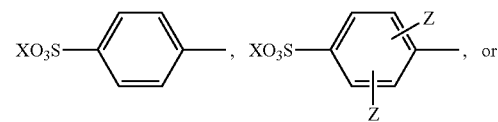

, or

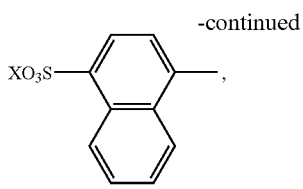

$R^2$ is

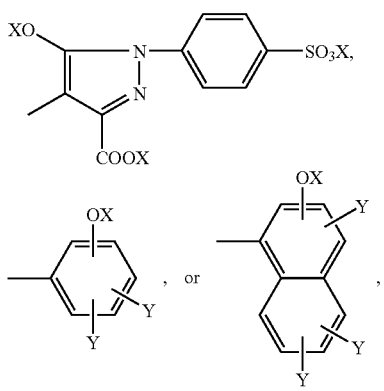

and in $R^1$ and $R^2$,

X is hydrogen, a halogen, sodium, or potassium,

Y is hydrogen or $SO_3X$,

Xs may be the same or different, Ys may be the same or different, and

Z is hydrogen, a methyl group, or a methoxy group, and Zs may be the same or different); and

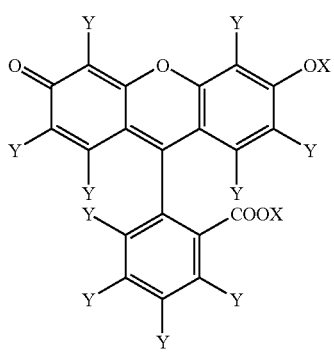

(II)

(in Formula (II),

X is hydrogen, a halogen, sodium, or potassium, and Xs may be the same or different, and Y is hydrogen, a halogen, sodium, or potassium, and Ys may be the same or different).

A method for measuring a target component of the present invention is a method for measuring a target component in a sample by detecting a phenothiazine-derivative color, comprising steps (A) to (E) below:

(A) a step of producing an oxidizing substance or reducing substance from the target component in the sample;

(B) a color-developer-adding step of adding, to the sample, a color-developer that produces a phenothiazine-derivative color through oxidation-reduction;

(C) a step of producing a phenothiazine-derivative color through oxidation-reduction between the oxidizing substance or reducing substance and the color-developer;

(D) a step of detecting a phenothiazine-derivative color using the method for detecting a phenothiazine-derivative color of the present invention, and measuring a presence/absence or an amount of the phenothiazine-derivative color produced; and (E) a step of determining a presence/absence or an amount of the target component in the sample based on a result of the measurement.

Furthermore, the method for measuring a target component of the present invention may be a method comprising steps (B') to (D') below instead of the steps (B) to (D):

(B') a step of adding a phenothiazine-derivative color as a color-developer to the sample;

(C') a step of causing oxidation-reduction between a reducing substance produced by the target component in the sample and the phenothiazine-derivative color; and (D') a step of detecting a phenothiazine-derivative color using the method for detecting a phenothiazine-derivative color of the present invention, and measuring a presence/absence or an amount of decrease in the added phenothiazine-derivative color.

A shifting agent of the present invention is a shifting agent that shifts an absorption spectrum of a phenothiazine-derivative color, comprising at least one color substance selected from the group consisting of a compound represented by Formula (I) above, a compound represented by Formula (II) above, and a flavonoid-based color.

A color-developer reagent of the present invention is a color-developer reagent used in the detection method of the present invention, comprising either one color-developer of a substrate that produces a phenothiazine-derivative color through oxidation-reduction or a phenothiazine-derivative color, and the shifting agent of the present invention.

According to the present invention, in the presence of the color substance, a phenothiazine-derivative color can be detected even at a wavelength longer than 590 to 670 nm, which is the original maximum absorption wavelength of a phenothiazine-derivative color. Thus, for example, even in the case where a sample contains a component that exhibits an absorption of around 570 to 670 nm, the influence thereof can be averted in the detection of a phenothiazine-derivative color. Furthermore, according to the present invention, for example, the light absorbance at 700 nm increases, and, thus, even an apparatus in which the detection wavelength is fixed to 700 nm can detect a phenothiazine-derivative color. In this manner, according to the method of the present invention, the conditions for detecting a phenothiazine-derivative color are improved, and, thus, the application range of a color-developer that produces a phenothiazine-derivative color and a phenothiazine-derivative color as a color-developer can be further increased compared with that of conventional methods. Accordingly, it can be said that this method is an extremely useful method, for example, in clinical tests and the like.

BEST MODE FOR CARRYING OUT THE INVENTION

Shifting Agent for Absorption Spectrum

Figure 1:
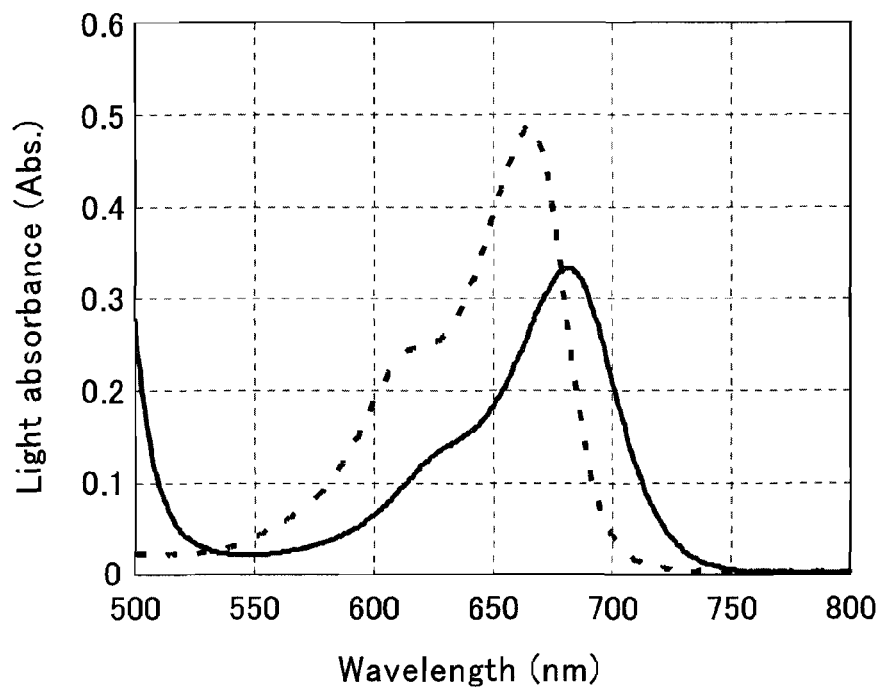
FIG. 1 shows a graph of a spectrum of methylene blue in the presence of tartrazine in Example 1 of the present invention.

The shifting agent of the present invention is a shifting agent that shifts an absorption spectrum of a phenothiazine-derivative color, comprising at least one color substance selected from the group consisting of a compound represented by Formula (I) above, a compound represented by Formula (II) above, and a flavonoid-based color.

As described above, in the presence of the phenothiazine-derivative color, the color substance can shift the absorption spectrum of the phenothiazine-derivative color toward the long-wavelength side. Accordingly, the color substance in the present invention can be used as an absorption spectrum-shifting agent that changes the absorption spectrum of the phenothiazine-derivative color as described above. Furthermore, in the present invention, "shift an absorption spectrum" refers to, for example, processing that shifts the original maximum absorption wavelength of the phenothiazine-derivative color toward the long-wavelength side, or processing that shifts the absorption spectrum toward the long-wavelength side without shifting the maximum absorption wavelength. The shifting agent of the present invention is preferably a substance having two negatively charged groups that are spaced apart from each other as appropriate. It is believed that these negatively charged groups and the positively charged Ns positioned on both sides of the phenothiazine framework are electrically bonded to extend the resonance structure, and, thus, shift occurs. Here, the present invention is not limited to this.

In the shifting agent of the present invention, the number of types of color substances may be one, or may be two or more.

 (I)

In Formula (I),
$R^1$ is

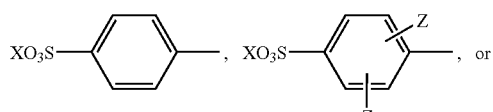

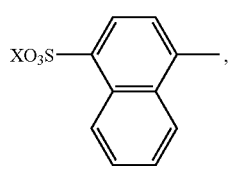

$R^2$ is

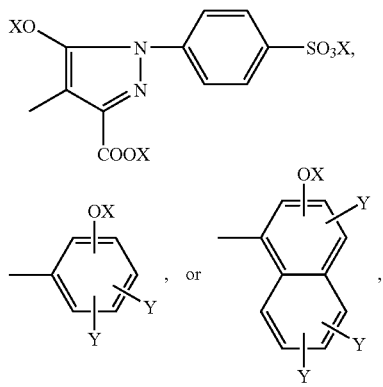

and in $R^1$ and $R^2$,

X is hydrogen, a halogen, sodium, or potassium,

Y is hydrogen or $SO_3X$,

Xs may be the same or different, and Ys may be the same or different, and

Z is hydrogen, a methyl group, or a methoxy group, and Zs may be the same or different.

Examples of

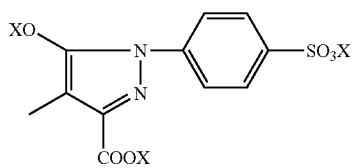

include

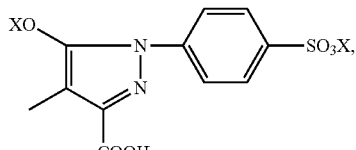

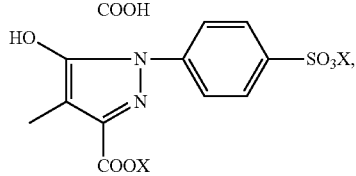

and the like.

Examples of

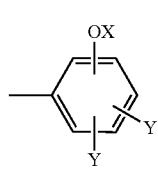

include

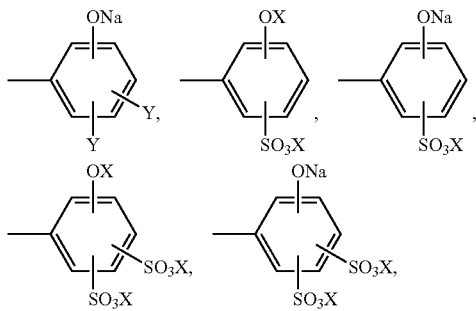

and the like.
Examples of

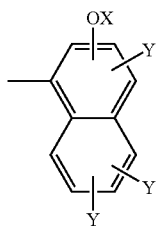

include

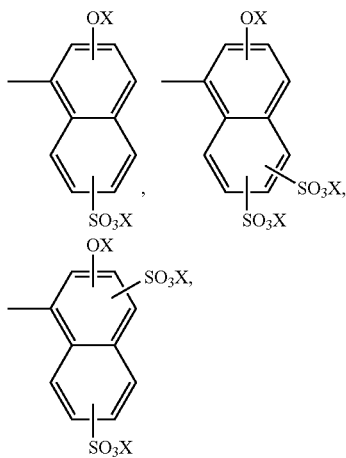

and the like.

Examples of the color substance represented by Formula (I) include 5-hydroxy-1-(4-sulfophenyl)-4-(4-sulfophenylazo)pyrazole-3-carboxylic acid and a salt (e.g., a trisodium salt) thereof, 6-hydroxy-5-(4-sulfophenylazo)-2-naphthalenesulfonic acid and a salt (e.g., a disodium salt) thereof, 3-hydroxy-4-(4-sulfonaphthylazo)-2,7-naphthalenedisulfonic acid (also referred to as "3-hydroxy-4-[(sulfonatonaphthalene-1-yl)diazenyl]naphthalene-2,7-disulfonic acid") and a salt (e.g., a trisodium salt) thereof, 7-hydroxy-8-(4-sulfonaphthylazo)-1,3-naphthalenedisulfonic acid and a salt (e.g., a trisodium salt) and hydrate (e.g., 11/2 hydrate) thereof, and the like. Examples of these salts and hydrates include commercially available tartrazine (Yellow No. 4), Yellow No. 5, Red No. 2, Red No. 40, Red No. 102, and the like. These color substances may be used for food.

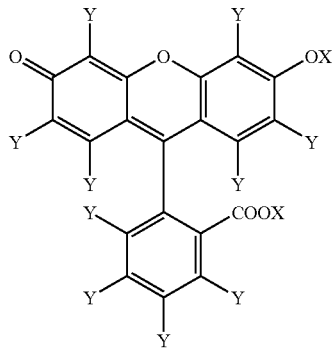
(II)

In Formula (II),
X is hydrogen, a halogen, sodium, or potassium, and Xs may be the same or different, and
Y is hydrogen, a halogen, sodium, or potassium, and Ys may be the same or different.

In the present invention, "halogen" refers to any halogen element. Examples of the halogen include fluorine, chlorine, bromine, and iodine.

Furthermore, examples of the color substance represented by Formula (II) include 3',6'-dihydroxy-2',4',5',7'-tetraiodospiro[isobenzofuran-1(3H), 9'-(9H)xanthene]-3-one and a salt (e.g., a disodium salt) and hydrate (e.g., a monohydrate) thereof, 3',6'-dihydroxy-2',4',5',7'-tetrabromo-4,5,6,7,-tetrachlorospiro[isobenzofuran-1(3H), 9'-[9H]xanthene]-3-one and a salt (e.g., a disodium salt) thereof, 4,5,6,7-tetrachloro-3',6'-dihydroxy-2',4',5',7'-tetraiodospiro[isobenzofuran-1 (3H),9'-[9H]xanthene]-3-one and a salt (e.g., a disodium salt) thereof, 2,4,5,7-tetrabromo-3,6-dihydroxyxanthene-9-spiro-1'-3H-isobenzofuran-3'-one and a salt (e.g., a disodium salt) thereof, 3,6-dihydroxyxanthene-9-spiro-1'-3'H-isobenzofuran-3'-one and a salt (e.g., a disodium salt) thereof, and the like. Examples of these salts and hydrates include Red No. 3, Red No. 104, Red No. 105, eosin (acid red 87), uranine, and the like. These color substances may be used for food.

Examples of the flavonoid-based color include a flavonoid, a flavonoid polymer, and the like. Examples of the flavonoid include a commercially available Japanese persimmon color (Japanese persimmon color from *Dipospyros kaki* THUMB.). Typically, such Japanese persimmon color mainly comprises a flavonoid extracted from fruits. Furthermore, examples of the flavonoid polymer include commercially available cacao color (Cacao color from *Theobroma cacao* LINNE). Typically, the cacao color mainly comprises an anthocyanin polymer. The anthocyanin polymer is represented, for example, by the following formula. In the following formula, n represents the degree of polymerization. Here, n is not particularly limited, but is, for example, 5 or more, and preferably 6 or more. The upper limit of n is not particularly limited. R represents glycoside galacturonic acid.

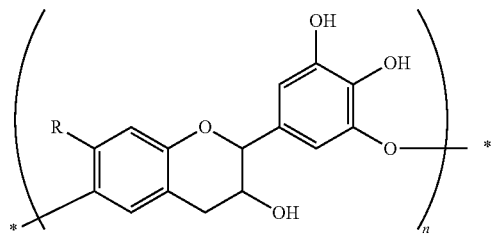

The phenothiazine-derivative color in the present invention is not particularly limited, but examples thereof include diaminophenothiazine and a derivative thereof.

Furthermore, examples of the phenothiazine-derivative color include a compound represented by Formula (III) below, a tautomer and stereoisomer thereof, and a salt thereof.

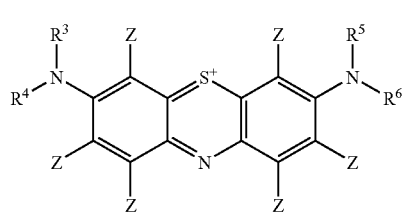

In Formula (III), $R^3$ to $R^6$ are each a hydrogen atom or an alkyl group, and may be the same or different. Examples of the alkyl group include a linear or branched alkyl group having 1 to 6 carbon atoms, and preferably include a methyl group. In Formula (III), each Z is a hydrogen atom, an alkyl group, a nitro group, an amino group, a halogen, a sulfo group, or a carboxyl group, and may be the same or different. In Z, examples of the alkyl group include a linear or branched alkyl group having 1 to 6 carbon atoms, and preferably include a methyl group.

Here, in the present invention, the colors represented by Formulae (I), (II), and (III) may be isomers thereof, such as a tautomer or stereoisomer (e.g., a geometrical isomer, a conformational isomer, and an optical isomer). Furthermore, in Formula (III), in the case of a salt, a counter ion is not particularly limited, but examples thereof include anions (negative ions), such as the hexafluorophosphate ion ($PF_6^-$), tetrafluoroboric acid ion ($BF_4^-$), hydroxide ion ($OH^-$), acetic acid ion, carbonic acid ion, phosphoric acid ion, sulfuric acid ion, nitric acid ion, halide ion, hypohalous acid ion, halous acid ion, halogen acid ion, perhalogen acid ion, trifluoromethanesulfonic acid ion ($OSO_2CF_3^-$), and tetrakispentafluorophenylborate ion $[B(C_6F_5)_4^-]$. Examples of the halide ion include fluoride ion ($F^-$), chloride ion ($Cl^-$), bromide ion ($Br^-$), iodide ion ($I^-$), and the like. Examples of the hypohalous acid ion include the hypofluorous acid ion, hypochlorous acid ion, hypobromous acid ion, hypoiodous acid ion, and the like. Examples of the halous acid ion include the fluorous acid ion, chlorous acid ion, bromous acid ion, iodous acid ion, and the like. Examples of the halogen acid ion include the fluoric acid ion, chloric acid ion, bromic acid ion, iodic acid ion, and the like. Examples of the perhalogen acid ion include the perfluoric acid ion, perchloric acid ion, perbromic acid ion, periodic acid ion, and the like.

In the present invention, "halogen" refers to any halogen element. Examples of the halogen include fluorine, chlorine, bromine, and iodine. Furthermore, in the present invention, "alkyl group" is not particularly limited. Examples of the alkyl group include the methyl group, ethyl group, n-propyl group, isopropyl group, n-butyl group, isobutyl group, sec-butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, and the like. Furthermore, in the present invention, in a case where there are isomers of a substituent or the like, any isomer may be used unless otherwise specified. For example, "propyl group" may refer to either n-propyl group or isopropyl group. Furthermore, "butyl group" may refer to any of n-butyl group, isobutyl group, sec-butyl group, and tertbutyl group.

Specific examples of the phenothiazine-derivative color include methylene blue, azure A, azure B, azure C, toluidine blue O, 1,9-dimethyl-3,7-bis(dimethylamino)phenothiazine salt, and methylene green represented by the following formulae.

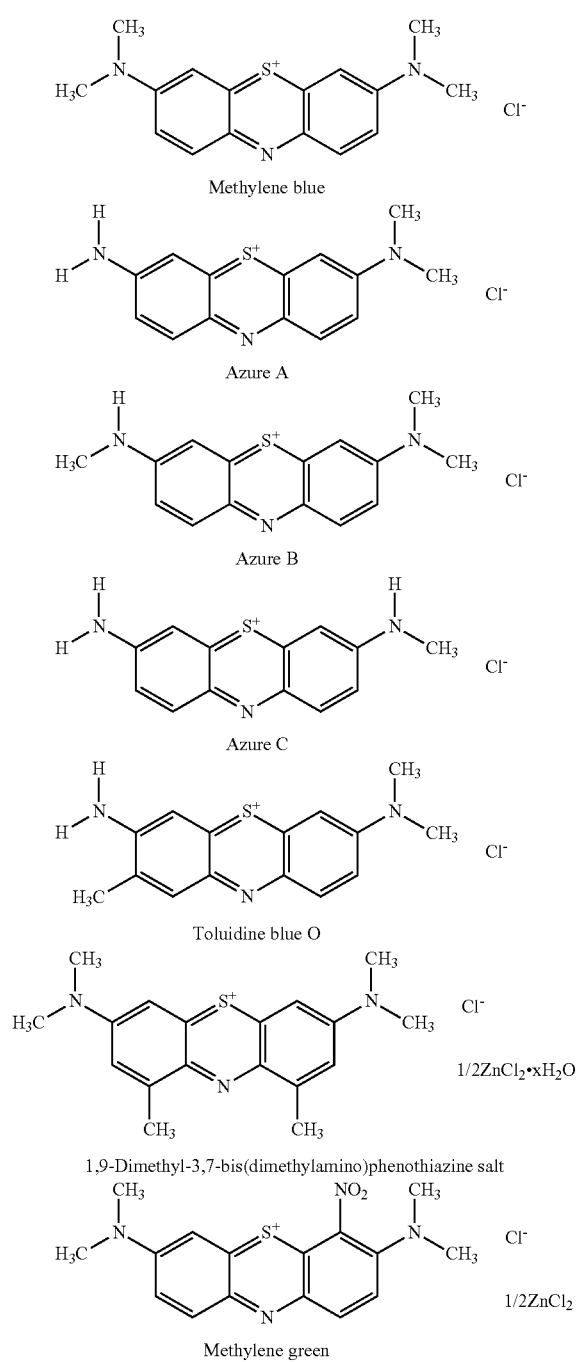

<Method for Detecting a Phenothiazine-Derivative Color>

A method for detecting a phenothiazine-derivative color in a reaction system by measuring a light absorbance comprises a step of detecting a phenothiazine-derivative color, wherein, in the detecting step, a phenothiazine-derivative color is detected in the presence of at least one color substance (the shifting agent of the present invention) selected from the group consisting of a compound represented by Formula (I) above, a compound represented by Formula (II) above, and a flavonoid-based color.

In the present invention, the color substance is as described above, and can be used as the shifting agent of the present invention. The color substance need only to be present in the reaction system during detection of the phenothiazine-derivative color, and, for example, may be added before the detecting step.

As described above, the phenothiazine-derivative color in the present invention is not particularly limited. A substance from which the phenothiazine-derivative color detected in the present invention is derived is not particularly limited, and examples thereof include a phenothiazine-derivative color derived from a color-developer that produces a phenothiazine-derivative color through oxidation-reduction, and a phenothiazine-derivative color itself added as the color-developer.

The color-developer that produces a phenothiazine-derivative color through oxidation-reduction is not particularly limited, but examples thereof include substrates that free (desorb) a phenothiazine-derivative color through oxidation or reduction.

Specific examples of a substrate that frees methylene blue, which is a phenothiazine-derivative color, through oxidation include 10-(carboxymethylaminocarbonyl)-3,7-bis(dimethylamino)phenothiazine and a salt (e.g., product name DA-67, manufactured by Wako Pure Chemical Industries, Ltd.) thereof, 10-(acetylaminocarbonyl)-3,7-bis(dimethylamino)phenothiazine and a salt thereof, 10-(phenylcarbonyl)-3,7-bis(dimethylamino)phenothiazine as described in Patent Document 3 and a salt thereof, and the like. Furthermore, 10-(3-(methylcarboxyamino)-hexamethyl-amino)-phenothiazine, 10-(3-(methylcarboxyamino)-4-methyl-phenyl)-amino)-phenothiazine, 10-((3-(methylcarboxyamino methyl)-phenyl)-methylamino)-phenothiazine, 10-(1-naphthaleneamino)-phenothiazine, 10-(methyl)-phenothiazine, 10-(phenylamino)-phenothiazine, and 10-(methylamino)-phenothiazine, which are the compounds No. II-4 to 9 and II-10 as described in Patent Document 4, and a salt thereof are included. Among these, 10-(carboxymethylaminocarbonyl)-3,7-bis(dimethylamino)phenothiazine salt is preferable because it is highly water-soluble.

Furthermore, in addition to the above, examples of a color-developer that produces methylene blue, which is a phenothiazine-derivative color, include leuco compounds, such as leucomethylene blue. Leucomethylene blue is a colorless compound (reduced-type), and is oxidized to methylene blue (oxidized-type). Thus, leucomethylene blue can be used, for example, as a substrate for detecting an oxidizing substance. In the present invention, for example, leucomethylene blue is added as the color-developer to the reaction system, methylene blue is produced through oxidation-reduction between the leucomethylene blue and an oxidizing substance in the reaction system, and then the light absorbance may be measured. Furthermore, examples of a color-developer that produces a phenothiazine-derivative color other than methylene blue include leuco compounds of various phenothiazine-derivative colors and the like.

This sort of color-developer typically is used when detecting the target component in the sample using oxidation-reduction. In the present invention, for example, the color-developer is added to the reaction system, and a phenothiazine-derivative color is produced (freed) from the color-developer through oxidation-reduction between the color-developer and an oxidizing substance or reducing substance in the reaction system. The amount of phenothiazine-derivative color freed corresponds to the amount of oxidizing substance or reducing substance, and, thus, the presence/absence or the amount of the oxidizing substance or reducing substance in the reaction system can be determined by detecting the presence/absence or the amount of phenothiazine-derivative color freed. The oxidizing substance or reducing substance may be produced, for example, from the target component in the sample through oxidation-reduction. Furthermore, in a case where the target component in the sample is an oxidizing substance or reducing substance, the target component without any treatment may be reacted with the color-developer, or an oxidizing substance or reducing substance further may be produced by the target component and reacted with the color-developer.

Here, as described above, in the present invention, "color-developer" refers to not only the substrate that produces a phenothiazine-derivative color that exhibits color through oxidation-reduction, but also a phenothiazine-derivative color itself. For example, in the case of methylene blue, as described above, methylene blue (oxidized-type) is reduced to colorless leucomethylene blue (reduced-type). Thus, methylene blue can be used, for example, as a substrate for detecting a reducing substance. Thus, in the present invention, for example, first, methylene blue is added as the color-developer to the reaction liquid, and leucomethylene blue is produced through oxidation-reduction between the added methylene blue and a reducing substance in the reaction system. Then, the presence/absence or the amount of decrease in the methylene blue may be measured by measuring the light absorbance of the methylene blue. That is to say, the presence/absence or the amount of reducing substance in the reaction system can be determined by measuring the decrease in the methylene blue added as the color-developer. Phenothiazine-derivative colors other than methylene blue also may be used in a similar manner, that is, for example, a phenothiazine-derivative color is added as the color-developer to the reaction liquid, oxidation-reduction is carried out between the added phenothiazine-derivative color and a reducing substance in the reaction system, and the presence/absence or the amount of decrease in the phenothiazine-derivative color is measured by measuring the light absorbance of the phenothiazine-derivative color.

In the present invention, the color substance may be added to the reaction system before the light absorbance of the phenothiazine-derivative color is measured. Accordingly, the color substance may be added to the reaction system either before or after oxidation-reduction that produces (frees) or loses a phenothiazine-derivative color, or may be added at the same time as or during oxidation-reduction. Here, the reaction system may be either a dry system, such as a test paper, or a wet system (solution), such as a reaction liquid.

The ratio of the color substance added is not particularly limited, but is, for example, 1 to 1000 mol, preferably 2 to 200 mol, and more preferably 4 to 100 mol, per 1 mol of phenothiazine-derivative color contained in the reaction system. Furthermore, the ratio of the color substance added can be determined, for example, according to the amount of color-developer added to the reaction liquid, and is, for example, 0.1 to 1000 mol, preferably 1 to 500 mol, and more preferably 4 to 300 mol, per 1 mol of color-developer.

Furthermore, the final concentration of the color substance in the reaction system is, for example, $1 \times 10^{-7}$ to 0.1 mol/L, preferably $2 \times 10^{-7}$ to 0.05 mol/L, and more preferably $5 \times 10^{-7}$ to 0.03 mol/L. The final concentration of the color-developer in the reaction liquid is not particularly limited, but is, for example, $1\times10^{-6}$ to 0.1 mol/L, preferably $5\times10^{-6}$ to 0.01 mol/L, and more preferably $5\times10^{-6}$ to 0.001 mol/L.

The maximum absorption wavelength of the phenothiazine-derivative color is known to be, typically, approximately 590 to 670 nm. Due to the spectrum, conventional methods merely can measure the light absorbance at a wavelength of approximately 550 to 680 nm. On the other hand, according to the method of the present invention, the spectrum of the phenothiazine-derivative color is shifted from the original spectrum toward the long-wavelength side in the presence of the color substance, and, thus, the measurement can be performed in a range with a wavelength longer than that in the above-described detection wavelength range in conventional methods. That is to say, the present invention can perform the measurement, for example, at 670 nm or more, 680 nm or more, and 690 nm or more. The detection wavelength in the present invention is, for example, 560 to 730 nm, and preferably 600 to 715 nm. In this manner, the method of the present invention can perform the measurement around 700 nm, which is not performed by conventional methods, and, thus, for example, this method also can be applied to present automatic analyzing apparatuses in which the detection wavelength is fixed to 700 nm. In a specific example, in the case where the light absorbance of a phenothiazine-derivative color solution (e.g., $10^{-6}$ mol/L) at 700 nm is measured in the presence of the color substance, the light absorbance obtained is, for example, 2 to 20 times the light absorbance at 700 nm in the absence of the color substance.

In a specific example, the maximum absorption wavelength of methylene blue is typically approximately 660 to 670 nm (e.g., approximately 666 nm), and conventional methods merely can measure the light absorbance, for example, at a wavelength of 600 to 680 nm. On the other hand, the method of the present invention can perform the measurement, for example, at 670 nm or more, 680 nm or more, and 690 nm or more. The detection wavelength of methylene blue in the present invention is, for example, 610 to 730 nm, preferably 650 to 715 nm, and more preferably 660 to 700 nm.

Azure A

The maximum absorption wavelength of azure A is typically approximately 630 to 640 nm (e.g., approximately 634 nm), and conventional methods merely can measure the light absorbance, for example, at a wavelength of 550 to 675 nm. On the other hand, the method of the present invention can perform the measurement, for example, at approximately 680 nm or more, approximately 690 nm or more, and approximately 700 nm or more, and the detection wavelength is, for example, approximately 590 to 715 nm, and preferably approximately 610 to 700 nm.

Azure B

The maximum absorption wavelength of azure B is typically approximately 610 to 620 nm (e.g., approximately 613 nm), and conventional methods merely can measure the light absorbance, for example, at a wavelength of 550 to 675 nm. On the other hand, the method of the present invention can perform the measurement, for example, at approximately 675 nm or more, approximately 690 nm or more, and approximately 700 nm or more, and the detection wavelength is, for example, approximately 575 to 710 nm, and preferably approximately 600 to 700 nm.

Azure C

The maximum absorption wavelength of azure C is typically approximately 610 to 625 nm (e.g., approximately 619 nm), and conventional methods merely can measure the light absorbance, for example, at a wavelength of 540 to 650 nm. On the other hand, the method of the present invention can perform the measurement, for example, at approximately 650 nm or more, approximately 660 nm or more, and approximately 670 nm or more, and the detection wavelength is, for example, approximately 580 to 690 nm, and preferably approximately 590 to 680 nm.

Toluidine blue O

The maximum absorption wavelength of toluidine blue O is typically approximately 625 to 635 nm (e.g., approximately 631 nm), and conventional methods merely can measure the light absorbance, for example, at a wavelength of 550 to 670 nm. On the other hand, the method of the present invention can perform the measurement, for example, at approximately 670 nm or more, approximately 690 nm or more, and approximately 700 nm or more, and the detection wavelength is, for example, approximately 600 to 700 nm, and preferably approximately 610 to 690 nm.

1,9-Dimethyl-3,7-bis(dimethylamino)phenothiazine salt

The maximum absorption wavelength of 1,9-dimethyl-3,7-bis(dimethylamino)phenothiazine salt is typically approximately 590 to 600 nm (e.g., approximately 592 nm), and conventional methods merely can measure the light absorbance, for example, at a wavelength of 520 to 675 nm. On the other hand, the method of the present invention can perform the measurement, for example, at approximately 675 nm or more, approximately 685 nm or more, and approximately 700 nm or more, and the detection wavelength is, for example, approximately 540 to 710 nm, and preferably approximately 570 to 700 nm.

Methylene Green

The maximum absorption wavelength of methylene green is typically approximately 605 to 615 nm (e.g., approximately 609 nm), and conventional methods merely can measure the light absorbance, for example, at a wavelength of 540 to 675 nm. On the other hand, the method of the present invention can perform the measurement, for example, at approximately 675 nm or more, approximately 690 nm or more, and approximately 700 nm or more, and the detection wavelength is, for example, approximately 550 to 710 nm, and preferably approximately 580 to 700 nm.

The method for detecting a phenothiazine-derivative color of the present invention can be applied to any method for performing measurement (e.g., qualitative or quantitative analysis) comprising a step of detecting a phenothiazine-derivative color. Thus, for example, this method is preferably applied to a method for performing a qualitative or quantitative analysis of the target substance, by producing or eliminating a phenothiazine-derivative color through oxidation-reduction, and measuring the presence/absence or increase/decrease in the amount of phenothiazine-derivative color.

<Method for Measuring a Target Component>

As described above, a first detection method of the present invention is a method for measuring a target component in a sample by detecting a phenothiazine-derivative color, comprising steps (A) to (E) below:

(A) a step of producing an oxidizing substance or reducing substance from the target component in the sample;

(B) a color-developer-adding step of adding, to the sample, a color-developer that produces a phenothiazine-derivative color through oxidation-reduction;

(C) a step of producing a phenothiazine-derivative color through oxidation-reduction between the oxidizing substance or reducing substance and the color-developer;

(D) a step of detecting a phenothiazine-derivative color using the method for detecting a phenothiazine-derivative color of the present invention, and measuring a presence/absence or an amount of the phenothiazine-derivative color produced; and (E) a step of determining a presence/absence or an amount of the target component in the sample based on a result of the measurement.

Furthermore, a second detection method of the present invention comprises steps (B') to (D') below instead of the steps (B) to (D):

(A) a step of producing an oxidizing substance or reducing substance from the target component in the sample;

(B') a step of adding a phenothiazine-derivative color as a color-developer to the sample;

(C') a step of causing oxidation-reduction between a reducing substance produced by the target component in the sample and the phenothiazine-derivative color;

(D') a step of detecting a phenothiazine-derivative color using the method for detecting a phenothiazine-derivative color of the present invention, and measuring a presence/absence or an amount of decrease in the added phenothiazine-derivative color; and (E) a step of determining a presence/absence or an amount of the target component in the sample based on a result of the measurement.

Here, the present invention detects a phenothiazine-derivative color in the presence of the shifting agent of the present invention (the color substance) as described above, and is not limited by any other step or condition.

The type of target component in the present invention is not particularly limited as long as, for example, measurement using detection of a phenothiazine-derivative color can be performed, and examples thereof include a target component from which an oxidizing substance or reducing substance can be produced through oxidation-reduction. In the case where the target component itself is an oxidizing substance or reducing substance, an oxidizing substance or reducing substance further may be produced by the target component as described above, or, for example, the step (A) may be omitted and the target component itself, which is an oxidizing substance or reducing substance, may be reacted with the color-developer in the step (B) or the step (B'). Specific examples of the target component include a glycated protein such as glycated hemoglobin (Hb) and glycated albumin, glycated peptide, glycated amino acid, glucose, uric acid, cholesterol, creatinine, sarcosine, glycerol, and the like.

The method is preferably applied to the measurement of glycated Hb, which is an important index indicating the state of a living body, among the above-mentioned target components. Examples of glycated Hb include Hb in which glucose is bonded to an α-amino group of a β-chain N-terminal amino acid (valine) (hereinafter, also referred to as "HbA1c") and Hb in which glucose is bonded to a side-chain amino group of lysine (hereinafter, also referred to as "GHbLys"). Then, the value of HbA1c (HbA1c %) is shown as the ratio of the amount of HbA1c to the amount of Hb (ratio, %), and is known to reflect the history of the in vivo blood glucose level (approximately 1 to 2 months). Furthermore, the value of GHbLys (GHbLys %) is shown as the ratio of the amount of GHbLys to the amount of Hb (ratio, %), and recently found by the present inventors to reflect the postprandial glucose level (patent pending). In this manner, the ratio of Hb glycated is a very important index in diagnosis, prevention, treatment, or the like of diabetes, and the measuring method is required to be improved further. Thus, the present invention is preferably applied to the measurement.

In the measuring method of the present invention, the type of sample is not particularly limited. Specific examples thereof include blood samples, such as whole blood, plasma, serum, and blood cell, in vivo samples, such as urine and cerebrospinal fluid, drinking water, food, and the like. In the case where the target component is a blood cell component, the sample can be prepared, for example, by hemolyzing blood cells or whole blood containing blood cells. The hemolytic method is not particularly limited, and examples thereof include a method using a difference in osmotic pressure, a method using ultrasonic waves, a treatment method using a surfactant, and the like. In the case where a difference in osmotic pressure is used, for example, whole blood (or blood cells) may be hemolyzed by adding purified water having a volume that is 2 to 100 times that of the whole blood (or blood cells).

In the measuring method of the present invention, the type of sample is not particularly limited, but application to blood samples is preferable because of the following reasons. As described above, the method for measuring a target component using the detection of a phenothiazine-derivative color commonly is used because the measurement can be performed on a relatively long-wavelength side. However, blood samples (particularly, samples containing a blood cell component) contain Hb, and, when the Hb is methylated, the samples exhibit an absorption at the original maximum absorption wavelength of a phenothiazine-derivative color. Thus, the detection of a phenothiazine-derivative color may be affected. On the other hand, according to the present invention, a phenothiazine-derivative color can be detected in a range with a longer wavelength, and, thus, the influence of methylated Hb as seen in conventional methods can be reduced, and the measurement precision can be further improved. Accordingly, when measuring, for example, glycated Hb or glycated albumin, which is a blood component, this method can be said to be particularly useful.

Next, the method for measuring a target component of the present invention will be described using an example in which the target component is glycated Hb, and HbA1c % is measured using a color-developer that frees a phenothiazine-derivative color through oxidation. Note that the present invention is not limited to this example.

(Protease Treatment)

First, glycated Hb in a sample is treated with protease. This step is not essential, but preferably is performed in order to allow fructosyl amino acid oxidase (hereinafter, referred to as "FAOD") in the subsequent step to act effectively on a glycated moiety of the Hb.

Examples of the protease include metalloprotease, serine protease, serine carboxypeptidase, proteinase K, bromelain, papain, porcine pancreas-derived trypsin, *Bacillus subtilis*-derived protease, *Aspergillus oryzae*-derived protease, and the like, and preferably include endoprotease. Examples of a commercially available protease include metalloprotease (manufactured by Arkray, Inc.), protease A "Amano" G (manufactured by Amano Enzyme Inc.), protease M "Amano" G (manufactured by Amano Enzyme Inc.), protease S "Amano" G (manufactured by Amano Enzyme Inc.), peptidase R (manufactured by Amano Enzyme Inc.), papain M-40 (manufactured by Amano Enzyme Inc.), a product named protease N (manufactured by Fluka), a product named protease N "Amano" (manufactured by Amano Enzyme Inc.), metalloproteinase derived from the genus *Bacillus* (manufactured by Toyobo Co., Ltd.: product name Toyoteam), and the like.

In particular, in the case where the β-chain N-terminal peptide of Hb is to be cut out, protease that catalyzes the cutting of the N-terminal peptide by specifically acting on the β-chain N-terminal (e.g., JP 2000-300294A, JP 2004-

344052A etc.) is preferable. Furthermore, examples of a protease that catalyzes the cutting of the β-chain N-terminal valine include the protease disclosed in International Publication No. 2000/50579 (Japanese Patent No. 3668801), International Publication No. 2000/61732, JP 2002-315600A, and the like.

The concentration of the protease added to this reaction liquid is, for example, 0.001 to 300,000 KU/L, and preferably 0.01 to 30,000 KU/L. In the case where the Hb concentration in the reaction liquid is 0.005 mM, the concentration of protease added is, for example, 0.01 to 300,000 KU/L, and preferably 0.05 to 30,000 KU/L. Regarding the protease activity "U", the amount of enzyme that increases the light absorbance at 275 nm, which corresponds to 1 μmol of tyrosine, at 35° C. in 1 minute is taken as 1 U.

The protease treatment preferably is performed, for example, in a buffer solution, and it is possible to use a Tris hydrochloric acid buffer solution, an EPPS buffer solution, a PIPES buffer solution, a phosphate buffer, an ADA buffer solution, a MES buffer solution, a MOPS buffer solution, a citric acid buffer solution, an acetic acid buffer solution, and the like. Furthermore, the pH of the protease reaction liquid is, for example, 4 to 10, and preferably 6 to 9. For example, the pH may be modulated using the above-mentioned buffer solutions.

The conditions of the protease treatment are not particularly limited, but the treatment temperature is, for example, 10 to 40° C., and preferably 25 to 37° C. The treatment time is, for example, approximately 1 to 100 minutes, and preferably 1 to 10 minutes.

Furthermore, this protease treatment may be performed, for example, in the presence of a promoting compound as shown below. When Hb is subjected to protease treatment in the presence of such a promoting compound, the protease treatment can be performed effectively in a shorter period of time. Furthermore, effective protease treatment can be performed, and, thus, for example, the amount of protease used for the treatment does not have to be increased.

As the promoting compound, for example, a compound represented by Formula (IV) below can be used.

R—X    (IV)

In Formula (IV), R is an alkyl group, substituted alkyl group, acyl group, or substituted acyl group having 9 or more carbon atoms. Specific examples thereof include a linear alkyl group and linear acyl group having 9 to 16 carbon atoms, a branched alkyl group and branched acyl group having to 40 carbon atoms, and comprising a main chain having 9 to 16 carbon atoms, and a linear alkyl group substituted with a cycloalkyl (e.g., comprising a cycloalkyl having 3 to 8 carbon atoms, and a linear chain, excluding cycloalkyl, having 4 to 13 carbon atoms), and the like. Examples of the cycloalkyl include cyclohexyl, cyclopentyl, cyclobutyl, and the like. In Formula (IV), X is a saccharide residue, and preferably is, for example, a monosaccharide or disaccharide residue. Examples of the monosaccharide include mannoside, glucoside, thioglucoside, and the like, and examples of the disaccharide include maltoside, fructopyranosyl-glucopyranoside, thiomaltoside, and the like. The structure of these saccharides may be any of α, β, D, and L. Furthermore, a hydrogen bonded to the ring structure of the saccharide or a hydrogen of an OH group may be substituted with, for example, Na, K, a halogen, or the like. Here, in the present invention, an atom (e.g., —O—, —S—, etc.) via which R and the ring structure of the saccharide residue are bonded is a constituent element of the saccharide residue.

Specific examples of the promoting compound of Formula (IV) include n-dodecyl-β-D-maltoside(n-dodecyl-β-D-maltopyranoside), 6-cyclohexylhexyl-β-D-maltoside, sucrose monolaurate(β-D-fructopyranosyl-α-D-glucopyranoside monododecanoate), n-decyl-β-D-maltoside(n-decyl-β-D-maltopyranoside), n-nonyl-β-D-thiomaltoside(n-nonyl-β-D-thiomaltoside), 5-cyclohexyl pentyl-β-D-maltoside, undecyl-β-D-maltoside, n-dodecyl-αβ-D-maltoside, hexadecyl-β-D-maltoside, 3-oxatridecyl-α-D-mannoside, and the like. The chemical formulae of these compounds are shown below. Among these, for example, n-dodecyl-β-D-maltoside, sucrose monolaurate, and hexadecyl-β-D-maltoside comprising R (alkyl chain) having 12 or more carbon atoms in Formula (IV) are preferable. Furthermore, in the case where R has the same number of carbon atoms (e.g., an alkyl group and an acyl group having the same number of carbon atoms), an acyl group is more preferable, and n-dodecyl-β-D-maltoside (n-dodecyl-β-D-maltopyranoside) is preferable.

The ratio of promoting compound added to the reaction liquid during the protease treatment is, for example, 0.01 to 200 mM, and preferably 0.4 to 100 mM. In the case where the Hb concentration in the reaction liquid is 0.005 mM, the ratio of the promoting compound added is, for example, 0.4 to 100 mM, and preferably 1 to 100 mM. Here, the order in which the promoting compound and the protease are added is not particularly limited, and they may be added simultaneously or may be added in a random order.

As described above, the conditions of the protease treatment are not particularly limited. However, in the presence of the promoting compound, the treatment time, in particular, the upper limit is not limited, and, for example, the protease treatment can be performed in approximately 0.1 to 60 minutes. The treatment time is, preferably 0.1 to 45 minutes, more preferably 0.2 to 20 minutes, and particularly preferably 0.2 to 5 minutes. In the case where the protease treatment is performed in the presence of the promoting compound, an amino acid or peptide can be more promptly cut out, and, thus, the cutting treatment can be performed sufficiently even in the above-described treatment time.

Furthermore, in addition to the compound of Formula (IV), examples of the promoting compound further include nitro compounds. They may be used alone, or in a combination of two or more types. Examples of the nitro compound include nitrous acid and a salt thereof. The nitrous acid salt is not particularly limited, but examples thereof include potassium nitrite, amyl nitrite, butyl nitrite, nitroglycerin, sodium nitrite, para-nitrochlorobenzene, trinitrotoluene, nitrobenzene, and the like. The ratio of the nitro compound added to the reaction liquid during the protease treatment is not particularly limited, but, in the case where the Hb concentration in the reaction liquid is 0.005 mM, the ratio of nitro compound added is, for example, preferably 0.005 mM or more, and more preferably 0.05 to 2 mM.

In addition to the above-described compounds, examples of the promoting compound include a tetrazolium compound. The tetrazolium compound is not particularly limited, but examples thereof include 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl)-2H-tetrazolium salt, 2-(2-methoxy-4-nitrophenyl)-3-(4-nitrophenyl)-5-(2,4-disulfophenyl)-2H-tetrazolium salt, 2-(4-iodophenyl)-3-(4-nitrophenyl)-5-phenyl-2H-tetrazolium salt, 3,3'-(1,1'-biphenyl-4,4'-diyl)-bis(2,5-diphenyl)-2H-tetrazolium salt, 3,3'-[3,3'-dimethoxy-(1,1'-biphenyl)-4,4'-diyl]-bis[2-(4-nitropenyl)-5-phenyl-2H-tetrazolium salt], 2,3-diphenyl-5-(4-chlorophenyl)tetrazolium salt, 2,5-diphenyl-3-(p-diphenyl)tetrazolium salt, 2,3-diphenyl-5-(p-diphenyl)tetrazolium salt, 2,5-diphenyl-3-(4-styrylphenyl)tetrazolium salt, 2,5-diphenyl-3-(m-tolyl)tetrazolium salt, 2,5-diphenyl-3-(p-tolyl)tetrazolium salt, 2,3-diphenyl-5-(2-thienyl)tetrazolium salt, 2-benzothiazoyl-3-(4-carboxy-2-methoxyphenyl)-5-[4-(2-sulfoethylcarbamoyl)phenyl]-2H-tetrazolium salt, 2,2'-dibenzothiazolyl-5,5'-bis[4-di(2-sulfoethyl)carbamoylphenyl]-3,3'-(3,3'-dimethoxy-4,4'-biphenylene)ditetrazolium salt, 3-(4,5-dimethyl-2-thiazoyl)-2,5-diphenyl-2H-tetrazolium salt, 2,3-diphenyl-5-cyanotetrazolium salt, 2,3-diphenyl-5-carboxytetrazolium salt, 2,3-diphenyl-5-methyltetrazolium salt, 2,3-diphenyl-5-ethyltetrazolium salt, and the like, and particularly preferably include 2-(4-iodophenyl)-3-(2,4-dinitrophenyl)-5-(2,4-disulfophenyl)-2H-tetrazolium salt. The tetrazolium compound acts as a promoting compound, and, in addition, for example, in the case of a sample (e.g., blood sample) containing a reducing substance such as ascorbic acid, the tetrazolium compound can avert the influence of oxidation-reduction. In order to avert such influence, the tetrazolium compound may be added to the sample before the subsequent FAOD treatment step. Here, since the tetrazolium compound also acts as a promoting compound as described above, it is preferably added before the protease treatment.

The amount of tetrazolium compound added is not particularly limited, but is, for example, preferably 0.001 to 100 µmol, more preferably 0.005 to 10 µmol, and particularly preferably, 0.01 to 1 µmol, per 1 µL of sample.

(FAOD Treatment Step)

Next, FAOD is added to the Hb fragments obtained through the protease treatment so as to act on the glycated moiety of N-terminal valine, and, thus, hydrogen peroxide, which is an oxidizing substance, is produced. In order to measure the HbA1c of glycated Hb, FAOD may act on the glycated moiety of the β-chain N-terminal valine, in the peptide containing β-chain N-terminal glycated valine or the glycated valine, in the Hb fragments obtained with protease. Here, as described above, the Hb fragments may be determined according to the selection of the type of protease used.

The FAOD is not particularly limited, but is preferably an enzyme (hereinafter, referred to as "FAOD-α") that acts on an amino acid or peptide having glycated α-amino group, and catalyzes a reaction that generates hydrogen peroxide and α-keto-aldehyde. This catalyst reaction can be represented, for example, by Formula (1).

$$R^1-CO-CH_2-NH-R^2+H_2O+O_2 \rightarrow R^1-CO-CHO+NH_2-R^2+H_2O_2 \quad (1)$$

In Formula (1), $R^1$ is a hydroxyl group, or a residue (saccharide residue) derived from a saccharide before glycation. The saccharide residue ($R^1$) is an aldose residue in the case where the saccharide before the reaction is aldose, and is a ketose residue in the case where the saccharide before the reaction is ketose. For example, in the case where the saccharide before the reaction is glucose, the structure after the reaction is a fructose structure due to Amadori rearrangement. In this case, the saccharide residue ($R^1$) is a glucose residue (aldose residue). The saccharide residue ($R^1$) can be represented, for example, as:

—[CH(OH)]$_n$—CH$_2$OH where n is an integer of 0 to 6.

In Formula (1), $R^2$ is not particularly limited, but is, for example, the amino acid residue or peptide residue represented by Formula (2).

—CHR$^3$—CO—R$^4$ (2)

In Formula (2), $R^3$ is an amino acid side-chain group, $R^4$ is a hydroxyl group, amino acid residue, or peptide residue, and can be represented, for example, by Formula (3). In Formula (3), n is an integer of 0 or more, and $R^3$ is an amino acid side-chain group as described above, where the amino acid side-chain groups may be the same or different.

—(NH—CHR$^3$—CO)$_n$—OH (3)

Examples of FAOD-α include the fructosyl amine oxidase as described in International Publication No. 2004/029251, the fructosyl amine oxidase as described in JP 2004-275013A and JP 2004-275063A, FAOD derived from the genus *Penicilium* (JP H8-336386A), and the like. When such FAOD is used, for example, even in the case where a moiety other than the β-chain N-terminal valine is glycated, the FAOD hardly acts on such a moiety other than the glycated moiety of valine, and, thus, HbA1c can be measured more precisely.

Here, the FAOD further may have substrate-specificity other than (1). Examples of such FAOD include FAOD (hereinafter, referred to as "FAOD-αS") that acts on both of the glycated α-amino group and the glycated amino acid side-chain group. Specific examples thereof include a product named FPOX-CE (manufactured by Kikkoman Corporation), a product named FPOX-EE (manufactured by Kikkoman Corporation), a commercially available product named FOD (manufactured by Asahi Kasei Corporation), FAOD derived from the genus *Gibberella* (JP H8-154672A), FAOD derived from the genus *Fusarium* (JP H7-289253A), FAOD derived from the genus *Aspergillus* (WO 99/20039), and the like. In the case of such FAOD, action on the other glycated moieties can be suppressed, for example, by appropriately selecting the type of protease and combining the FAOD with protease that specifically cuts the β-chain N-terminal amino acid or peptide.

The FAOD treatment preferably is performed in a buffer solution as in the protease treatment. The buffer solution is not particularly limited, but it is possible to use the buffer solutions described for the protease treatment. The conditions of the FAOD treatment are not particularly limited, but the pH of the reaction liquid is, for example, 6 to 9, and the treatment temperature is, for example, 10 to 38° C., and preferably 25 to 37° C. The treatment time is not particularly limited either, and is, for example, 0.1 to 60 minutes, and preferably 0.1 to 5 minutes.

The concentration of the FAOD added to the reaction liquid during the FAOD treatment is, for example, 0.01 to 50 KU/L, and preferably 0.5 to KU/L. Regarding the FAOD activity "U", the amount that produces 1 µmol of hydrogen peroxide in 1 minute using fructosyl valine as a substrate is taken as 1 U.

(Phenothiazine-Derivative Color-Producing Step)

Next, the above-described color-developer is added to the reaction liquid, and oxidation-reduction is carried out between the hydrogen peroxide formed by the FAOD treatment and the color-developer. Through this reaction, the color-developer is oxidized, and, thus, a phenothiazine-derivative color is produced.

In the oxidation-reduction, an oxidizing enzyme preferably is used as a catalyst, and examples thereof include peroxidase (POD). This reaction preferably is performed in a buffer solution as in the FAOD treatment, and it is possible to use the buffer solutions described above. The conditions of the POD treatment are not particularly limited, but the pH of the reaction liquid is, for example, 5 to 9, and the treatment temperature is, for example, 10 to 40° C., and preferably 25 to 37° C. The treatment time is not particularly limited either, and is, for example, 0.1 to 5 minutes. The concentration of POD added to the reaction liquid is, for example, 0.01 to 300

KU/L, and preferably 0.5 to 40 KU/L. Regarding POD activity "U", the amount that oxidizes 1 μmol of guaiacol in 1 minute is taken as 1 U.

Furthermore, the ratio of the color-developer added to the reaction liquid is, for example, 0.001 to 10 mM, and preferably 0.005 to 2 mM.

(Light Absorbance Measuring Step)

Next, after the above-described color substance is added to the reaction liquid, the light absorbance of the phenothiazine-derivative color is measured. As described above, this color substance may be added at any time as long as it is added before measuring the light absorbance. For example, the color substance may be added either before or after the phenothiazine-derivative color-producing step, or may be added at the same time as the addition of the color-developer or oxidizing enzyme.

The ratio of the color substance added is not particularly limited, but is, for example, 0.1 to 1000 mol, preferably 1 to 500 mol, and more preferably 1 to 300 mol, per 1 mol of color-developer. Furthermore, the final concentration in the reaction liquid is, for example, 0.001 to 100 mmol/L, preferably 0.005 to 50 mmol/L, and more preferably 0.01 to 10 mmol/L.

Spectrophotometers, other conventionally known detecting apparatuses, and the like can be used for measuring the light absorbance. The light absorbance of a reaction liquid indicates the amount of phenothiazine-derivative color produced, the amount of phenothiazine-derivative color produced corresponds to the amount of hydrogen peroxide, and the amount of hydrogen peroxide corresponds to the amount of β-chain N-terminal valine glycated in Hb. Accordingly, the amount of Hb glycated (HbA1c concentration) can be obtained indirectly by measuring the light absorbance. Moreover, the HbA1c % can be obtained by measuring the total amount of Hb (Hb concentration) in the sample, and calculating the ratio (percentage) between the amount of β-chain N-terminal valine glycated (HbA1c concentration) in the Hb and the total amount of Hb (Hb concentration) in the sample as shown in the following formula. Here, the amount of Hb can be measured using conventionally known methods or commercially available reagent kits.

HbA1c %=(amount of β-chain N-terminal valine glycated/amount of Hb)×100

The amount of Hb glycated may be calculated based on the light absorbance, for example, using a calibration curve obtained by plotting the relationship between an already known amount of β-chain N-terminal glycated in Hb and the light absorbance. For example, the light absorbance of an Hb standard solution in which the amount of β-chain N-terminal glycated is already known is measured as described above, and a calibration curve indicating the relationship between the measured value of this standard solution and already known glycation amount is developed. Then, as described above, the amount of β-chain N-terminal glycated can be calculated by substituting a measured light absorbance for this calibration curve.

Furthermore, the GHbLys % of glycated Hb can be measured, for example, as in the HbA1c % measurement except for the following points.

The proteases described above may be used. Among these, in order to cut out lysine or lysine peptide, for example, the protease as described in International Publication No. 2002/006519 is preferably used.

The FAOD is not particularly limited, but is preferably an enzyme (FAOD-S) that acts on an amino acid or peptide having a glycated amino group (e.g., ε-amino group) of an amino acid side-chain, and catalyzes the reaction represented by Formula (1').

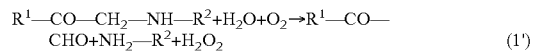
$$R^1—CO—CH_2—NH—R^2+H_2O+O_2 \rightarrow R^1—CO—CHO+NH_2—R^2+H_2O_2 \quad (1')$$

In Formula (1'), $R^1$ is similar to $R^1$ of Formula (1), and $R^2$ can be represented by Formula (4'). In Formula (4'), "—$(CH_2)_4$—" is a moiety other than a glycated amino group, among lysine side-chain groups.

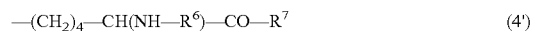
$$—(CH_2)_4—CH(NH—R^6)—CO—R^7 \quad (4')$$

Furthermore, in Formula (4'), $R^6$ is hydrogen, an amino acid residue, or a peptide residue, and can be represented, for example, by Formula (5'). Here, in Formula (5'), n is an integer of 0 or more, and $R^3$ is an amino acid side-chain group, where the amino acid side-chain groups may be the same or different.

$$—(CO—CR^3H—NH)_n—H \quad (5')$$

Furthermore, in Formula (4'), $R^7$ is a hydroxyl group, amino acid residue, or peptide residue, and can be represented, for example, by Formula (6'). Here, in Formula (6'), n is an integer of 0 or more, and $R^3$ is an amino acid side-chain group as described above, where the amino acid side-chain groups may be the same or different.

$$—(NH—CHR^3—CO)_n—OH \quad (6')$$

Examples of the FAOD-S that specifically acts on the glycated amino acid side-chain include FAOD derived from the genus *Fusarium* (the Society for Biotechnology, Japan Annual Meeting of H12 (2000) "Conversion of substrate-specificity of *Fusarium oxysporum*-derived amino acid oxidase; Maki Fujiwara et al."), and the like. Here, the FAOD further may have substrate-specificity other than Formula (1'), and it is also possible to use the FAOD-αS described above. In the case of such FAOD, action on the other glycated moieties can be suppressed, for example, by selecting protease (e.g., protease that specifically cuts lysine or peptide containing lysine) that does not produce a glycated amino acid having a glycated N-terminal amino group at the a position, such as the protease as stated in International Publication No. 2002/006519, and combining the FAOD therewith.

The GHbLys % can be obtained by measuring the light absorbance to obtain indirectly the amount of Lys side-chain amino group glycated (GHbLys concentration) of Hb, and calculating the ratio (percentage) between the amount of Lys side-chain amino group glycated (GHbLys concentration) and the total amount of Hb (Hb concentration) in the sample as shown in the following formula.

GHbLys %=(amount of Lys side-chain amino group glycated/amount of Hb)×100

Here, in the measurement of the ratio of Hb glycated (%), the treatment steps may be performed separately as described above, or may be simultaneously performed as long as the measurements are not affected. Specifically, for example, the treatments can be simultaneously performed in the following combinations. Furthermore, the order in which protease, FAOD, POD, and the color development substrate are added is not particularly limited. Among these, the color substance may be added in any step as long as it is added before the light absorbance of the phenothiazine-derivative color is measured.

1: hemolyzation treatment+protease treatment
2: protease treatment+FAOD treatment
3: FAOD treatment+POD treatment
4: protease treatment+FAOD treatment+POD treatment <Color-Developer Reagent>

The color-developer reagent of the present invention is a color-developer reagent used in the method for detecting a phenothiazine-derivative color of the present invention or the method for measuring a target component of the present invention, comprising either one color-developer of a compound that produces a phenothiazine-derivative color through oxidation-reduction or a phenothiazine-derivative color, and the shifting agent of the present invention (the above-described color substance).

The ratio of the color-developer and the color substance added to the color-developer reagent is not particularly limited, but the color substance is added in an amount of, for example, 0.1 to 1000 mol, preferably 1 to 500 mol, and more preferably 4 to 300 mol, per 1 mol of color-developer. Furthermore, the concentration of the color-developer and the color substance in the color-developer reagent is not particularly limited, and can be determined appropriately, for example, in view of the final concentration after being added to the reaction system, the dilution ratio due to addition to the reaction system, and the like.

The color-developer reagent may be dry (solid) or wet (liquid). In the case where the reaction system to which this reagent is added is liquid, for example, the reagent may be dissolved in an appropriate solvent to form a liquid reagent in use, or may be stored in a liquid form and used. The color substances, in particular, 5-hydroxy-1-(4-sulfophenyl)-4-(4-sulfophenylazo)pyrazole-3-carboxylic acid and a salt thereof, Yellow No. 5, Red No. 2, and the like preferably are applied in a liquid reagent. In the case where this color substance in a liquid form is brought together with the color-developer, due to the presence of the color substance, for example, the irradiation of light onto the color-developer in the liquid is blocked, and natural color development of the color-developer is suppressed. Thus, according to the present invention, the color-developer reagent can be stored in a liquid form for a long period of time, and the present invention is suitable particularly when using a light-unstable color-developer, such as DA-67.

The pH of the color-developer reagent is not particularly limited, and can be determined appropriately according to the type of color-developer, the pH condition of the reaction system in the target-measuring method, and the like. Specifically, the pH is, for example, 4 to 9, and preferably 5 to 9. Furthermore, in the case where the color-developer is 10-(carboxymethylaminocarbonyl)-3,7-bis(dimethylamino) phenothiazine salt (product name DA-67; manufactured by Wako Pure Chemical Industries, Ltd.), the pH is, for example, 4 to 10, and preferably 5 to 9.

The color-developer reagent of the present invention may be, for example, a reagent containing only the color-developer and the shifting agent of the present invention (the color substance), and further may contain various enzymes or additives, for example, according to the target-measuring method.

The color-developer reagent of the present invention will be described using an example in which this reagent is used in the above-described method for measuring glycated Hb. Note that the present invention is not limited to this example.

As described above, in the measurement of glycated Hb (measurement of glycation ratio), for example, protease, FAOD, POD, and the color-developer are used, but a first reagent shown below and a second reagent, which is the color-developer reagent of the present invention, can be used in combination.

The first reagent is, for example, a reagent containing FAOD and POD, or may be a reagent further containing a buffer, a surfactant for hemolyzing blood cells, a promoting compound that promotes protease treatment, and the like. The concentration of these components contained is not particularly limited, but, for example, in a case where the final dilution factor of the first reagent in the reaction system is set to 1.3 times, 0.3 to 10 KU/L of FAOD, 1 to 50 KU/L of POD, 10 to 200 mmol/L of buffer, 0.1 to 10 g/L of surfactant, and 0.1 to 10 g/L of promoting compound are contained, and the pH is 5 to 8.

The second reagent is, for example, a reagent containing a color substance, protease, and a color-developer, or may be a reagent further containing a buffer, salts of calcium chloride or the like, hexadecyltrimethylammonium chloride, and the like. The concentration of these components contained is not particularly limited, but, for example, in a case where the final dilution factor of the second reagent in the reaction system is set to 5.3 times, 10 to 1000 mg/L of color substance, 100 to 5000 KU/L of protease, 0.005 to 0.1 mmol/L of color-developer, 10 to 300 mmol/L of buffer, 0.5 to 20 mmol/L of calcium chloride, and 0.1 to 3 mmol/L of hexadecyltrimethylammonium chloride are contained, and the pH is 4 to 7.

The color-developer reagent of the present invention can be used as a constituent reagent of a reagent kit used in the method for detecting a phenothiazine-derivative color or the method for measuring a target component of the present invention. The reagent kit in the present invention contains the color-developer reagent of the present invention, and specific examples thereof include a reagent kit containing the first reagent and the second reagent, which is the color-developer reagent of the present invention.

Furthermore, according to the color-developer reagent of the present invention, when the shifting agent of the present invention (the color substance) is used together with the color-developer, for example, the natural occurrence of a phenothiazine-derivative color can be suppressed. Thus, the shifting agent of the present invention can be used, for example, as an inhibitor that suppresses the natural occurrence of a phenothiazine-derivative color from the color-developer. In the case where the color substance is used as the inhibitor, as described above, the ratio or concentration of the color-developer and the color substance contained in the color-developer reagent is not particularly limited.

<Method for Shifting an Absorption Spectrum>

The shifting method of the present invention is a method for shifting an absorption spectrum of a phenothiazine-derivative color in a reaction system, comprising adding a color substance (the shifting agent of the present invention) to the reaction system. As described above, the shifting agent of the present invention can shift the absorption spectrum of the phenothiazine-derivative color toward the long-wavelength side. A specific method is, for example, similar to the method for detecting a phenothiazine-derivative color of the present invention.

Hereinafter, the present invention will be described in more detail by way of examples, but the present invention is not limited to these.

EXAMPLE 1

Various shifting agents and methylene blue were used together, and it was confirmed whether or not a light absorbance peak in methylene blue was shifted or the spectrum was shifted toward the long-wavelength side.

(Shifting Agent)

| | |
|---|---|
| No. 1 | Tartrazine |
| No. 2 | Food additive, Food Yellow No. 5 |
| No. 3 | Food additive, Food Red No. 2 |
| No. 4 | Food additive, Food Red No. 3 |
| No. 5 | Food additive, Food Red No. 102 |
| No. 6 | Food additive, Food Red No. 104 |
| No. 7 | Food additive, Food Red No. 105 |
| No. 8 | Cacao color (manufactured by Kanto Chemical Co., Inc.) |
| No. 9 | Japanese persimmon color (manufactured by Kanto Chemical Co., Inc.) |

(Reaction Liquid Formulation)

| | |
|---|---|
| Methylene blue | 0.4 mg/L |
| MOPS | 300 mmol/L (pH 6.5) |
| Shifting agent | 300 mg/L |

Figure 2:
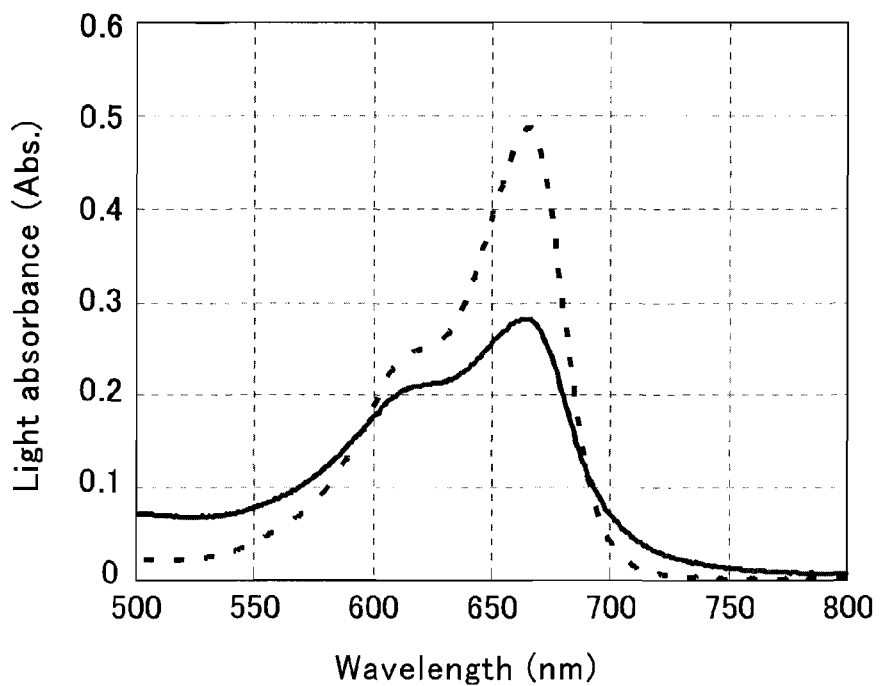
FIG. 2 shows a graph of a spectrum of methylene blue in the presence of cacao color in Example 1 of the present invention.

The spectrum of the reaction liquid was measured using a spectrophotometer (product name HITACHI U-3300: manufactured by Hitachi, Ltd.), and the maximum absorption wavelength, the maximum light absorbance, and the light absorbance at 700 nm in the spectrum of methylene blue were confirmed. Furthermore, measurement was performed in a similar manner also for a reaction liquid to which no shifting agent was added, as Comparative Example 1. Table 1 shows the results. Furthermore, FIGS. 1 and 2 show the spectra of the reaction liquids (example) containing the shifting agent No. 1 (tartrazine), or the shifting agent No. 8 (cacao color), and a reaction liquid to which no shifting agent was added (comparative example). Here, in FIGS. 1 and 2, the solid line shows the results for the example, and the dotted line shows the results for the comparative example.

TABLE 1

| Shifting agent No. | Maximum absorption wavelength (nm) | Maximum light absorbance (Abs.) | Light absorbance at 700 nm (Abs.) |
|---|---|---|---|
| Com. Ex. 1 | — | 666 | 0.488 | 0.043 |
| Ex. 1 | 1 | 682 | 0.333 | 0.209 |
| | 2 | 674 | 0.315 | 0.168 |
| | 3 | 686 | 0.233 | 0.179 |
| | 4 | 666 | 0.221 | 0.114 |
| | 5 | 670 | 0.317 | 0.124 |
| | 6 | 664 | 0.331 | 0.078 |
| | 7 | 666 | 0.295 | 0.072 |
| | 8 | 664 | 0.282 | 0.071 |
| | 9 | 663 | 0.270 | 0.074 |

As shown in Table 1, in every case where the shifting agent was used, the tendency was observed for the maximum absorption wavelength that exhibited the maximum light absorbance to be shifted toward the long-wavelength side, or the spectrum to be shifted overall toward the long-wavelength side although the maximum absorption wavelength was not changed. The former phenomenon was observed when using the shifting agent Nos. 1 to 3 and 5. More specifically, as represented in FIG. 1, in the reaction liquid using the shifting agent No. 1, the maximum absorption wavelength was shifted from 666 nm toward the long-wavelength side, and the light absorbance at 700 nm was increased to approximately 5 times that in Comparative Example 1, that is, the light absorbance could be measured sufficiently. Furthermore, the latter phenomenon was observed when using the shifting agent Nos. 4 and 6 to 9. More specifically, as represented in FIG. 2, in the reaction liquid using the shifting agent No. 8, the maximum absorption wavelength was 664 nm, but the light absorbance at 664 nm was decreased, and the spectrum was shifted overall toward the long-wavelength side. Thus, the light absorbance at 700 nm was increased compared with that in Comparative Example 1. Here, in a light absorbance measurement, typically, a light absorbance of approximately 0.05 can be regarded as a sufficiently reliable measured value. Thus, according to this example, it is determined that a sufficient measured value was obtained at 700 nm.

EXAMPLE 2

The HbA1c % was measured using a color-developer DA-67 that produces methylene blue through oxidation and the shifting agents of Example 1.

(Samples)

The following products diluted 27 times with the following diluents were used as samples (hereinafter, respectively referred to as "Low", "Medium", and "High"). Furthermore, purified water was used as a control.

Low: IFCC control Barcelona, Low HbA1c, Normal Hemoglobin (HbA1c %=3.2%)

Medium: IFCC control Barcelona, Medium HbA1c, Medium Hemoglobin (HbA1c %=5.1%)

High: IFCC control Barcelona, High HbA1c, Normal Hemoglobin (HbA1c %=7.5%)

TABLE 2

(Diluents)

| | |
|---|---|
| PIPES | 30 mmol/L (pH 7) |
| n-Dodecyl-αβ-D-maltoside | 0.5 g/L |
| $KNO_2$ | 35 mM |

(Method)

First, 6.5 μL of each sample and 6.5 μL of purified water were mixed, and the mixture was further mixed with 78 μL of the first reagent (R1) described below. This mixed liquid was incubated at 37° C. for 5 minutes, and then 19.5 μL of the second reagent (R2) described below was added, and protease treatment and color-developing reaction were carried out at 37° C. Then, a light absorbance ($A_0$) at a wavelength of 658 nm and a light absorbance ($A_0'$) at a wavelength of 694 nm in the reaction liquid immediately before adding the second reagent and a light absorbance ($A_5$) at a wavelength of 658 nm and a light absorbance ($A_5'$) at a wavelength of 694 nm in the reaction liquid at 5 minutes after adding the second reagent were measured using an automatic biochemical analyzing apparatus (product name JCA-BM8: manufactured by JEOL Ltd.), and the differences ($A_5$-$A_0$) and ($A_5'$-$A_0'$) were obtained. Here, as Comparative Example 2, the second reagent to which no shifting agent was added was used, and the same measurement was performed. Table 4 shows the results.

TABLE 3

(First Reagent: R1)

| | |
|---|---|
| FPOX-CE (manufactured by Kikkoman Corporation) | 1.5 KU/L |
| POD | 10 KU/L |
| PIPES | 30 mmol/L (pH 7) |
| EMULGEN A-500 (manufactured by Kao Corporation) | 0.05 g/L |
| n-Dodecyl-αβ-D-maltoside | 2.5 g/L |

TABLE 3-continued (Second Reagent: R2)

| | |
|---|---|
| Shifting agents (Nos. 1 to 9) | predetermined amount |
| Metalloprotease (manufactured by Arkray, Inc.) | 1800 KU/L |
| $CaCl_2$ | 5 mmol/L |
| Tris-HCl | 70 mmol/L |
| MES | 30 mmol/L (pH 5.5) |
| Hexadecyltrimethylammonium chloride | 0.2 g/L |
| DA-67 (manufactured by Wako Pure Chemical Industries, Ltd.) | 0.03 mmol/L |

*R2 was used after storage at 5° C. for 40 days in a state where light was blocked after preparation.

(Shifting Agent)

No. 1 Tartrazine (manufactured by Kishida Chemical Co., Ltd.) 100 mg/L

No. 2 Tartrazine (manufactured by Kishida Chemical Co., Ltd.) 200 mg/L

No. 3 Food additive, Food Yellow No. 4 (manufactured by Tokyo Chemical Industry Co., Ltd.) 100 mg/L

TABLE 4

| | Shifting agent No. | Wavelength (nm) | 658 nm ($A_5$-$A_0$) and 694 nm ($A_5'$-$A_0'$) | | | |
|---|---|---|---|---|---|---|
| | | | $H_2O$ | Low | Medium | High |
| Com. Ex. 2 | — | 658 | 0.024 | 0.034 | 0.045 | 0.058 |
| | | 694 | 0.004 | 0.005 | 0.007 | 0.009 |
| Ex. 2 | 1 | 658 | 0.022 | 0.033 | 0.042 | 0.052 |
| | | 694 | 0.013 | 0.015 | 0.020 | 0.026 |
| | 2 | 658 | 0.019 | 0.029 | 0.038 | 0.048 |
| | | 694 | 0.011 | 0.013 | 0.018 | 0.024 |
| | 3 | 658 | 0.041 | 0.053 | 0.062 | 0.072 |
| | | 694 | 0.024 | 0.026 | 0.031 | 0.037 |

As shown in Table 4, in Comparative Example 2 to which no shifting agent was added, the light absorbance at 658 nm ($A_5$-$A_0$) increased by a difference of approximately 0.01 as the HbA1c % of the samples increased (Low→Medium→High), but little change was seen in the light absorbance at 694 nm ($A_5'$-$A_0'$). Furthermore, even in the sample High having a high HbA1c %, the difference in light absorbance at 694 nm was 0.009, which is not of a satisfactory order to be reliable as a measured value (approximately 0.01 or more). On the other hand, for Example 2 to which the shifting agent was added, in every case where the shifting agent was used, the light absorbance at 694 nm ($A_5'$-$A_0'$) increased by a difference of 0.005 to 0.006 as the HbA1c % of the samples increased (Low→Medium→High). Moreover, even in the sample Low having the lowest HbA1c %, the difference in light absorbance was 0.01 or more, which is of a satisfactory order to be sufficiently reliable as a measured value. As a result, it was found that, when the above-described shifting agent is used in the detection of methylene blue, methylene blue can be detected at a wavelength longer than around 660 nm in conventional examples, and HbA1c % can be measured using the detection of methylene blue on the long-wavelength side.

EXAMPLE 3

Various phenothiazine-derivative colors and various shifting agents were used together, and it was confirmed whether or not a light absorbance peak was shifted or a spectrum was shifted toward the long-wavelength side in the color.

(Phenothiazine Derivative Solutions)

The following derivatives were dissolved in purified water at a ratio of 1 mmol/mL.

Methylene blue (Tokyo Chemical Industry Co., Ltd.)
Azure C (Fluka)
Azure A (Fluka)
1,9-Dimethyl-phenothiazine (1,9-dimethyl-3,7-bis(dimethylamino)phenothiazine salt, Sigma)
Toluidine blue O (Sigma)
Azure B (Wako Pure Chemical Industries, Ltd.)
Methylene green (MP Biomedica)

(Color Substance Solutions)

The following color substances were dissolved in purified water at a ratio of 10 mmol/mL.

| | |
|---|---|
| No. 1 | tartrazine |
| No. 2 | food additive, Food Yellow No. 5 |
| No. 3 | food additive, Food Red No. 2 |

(Buffer Solutions)

| | |
|---|---|
| MES-NaOH buffer solution | 30 mmol/mL pH 5.8 |
| MOPS-NaOH buffer solution | 30 mmol/mL pH 7.6 |

TABLE 5

(Reaction Liquid Formulations)

| | Control Ex. | Ex. |
|---|---|---|
| Phenothiazine derivative solutions | 0.05 mL | 0.05 mL |
| Color substance solutions | 0 mL | 0.05 mL |
| Buffer solutions | 3 mL | 2.95 mL |

The spectra of the reaction liquids immediately after preparation were measured using a spectrophotometer (product name V-550: manufactured by JASCO Corporation), and the maximum absorption wavelengths and the light absorbances at 700 nm were confirmed. Furthermore, measurement was performed in a similar manner also for a reaction liquid to which no color substance was added, as a comparative example.

Table 6 shows the maximum absorption wavelengths in the reaction liquids. Here, in Table 6, the numerical values in parentheses show the differences between the maximum absorption wavelength of the control and that of the example. As shown in Table 6, all phenothiazine-derivative colors could shift the maximum absorption wavelength toward the long-wavelength side in the presence of each color substance, compared with that of the control.

TABLE 6

| Phenothiazine-derivative color | Maximum absorption wavelength (nm) | | | |
|---|---|---|---|---|
| | Control | Tartrazine | Yellow No. 5 | Red No. 5 |
| Buffer solution (pH 5.8) | | | | |
| Methylene blue | 664 | 681 (17) | 688 (24) | 696 (32) |
| Azure C | 619 | 637 (18) | 642 (23) | 649 (30) |
| Azure A | 634 | 652 (18) | 657 (23) | 668 (34) |

TABLE 6-continued

| Phenothiazine-derivative color | Maximum absorption wavelength (nm) | | | |
|---|---|---|---|---|
| | Control | Tartrazine | Yellow No. 5 | Red No. 5 |
| 1,9-Dimethyl-phenothiazine | 592 | 664 (72) | 673 (81) | 683 (91) |
| Toluidine blue O | 631 | 649 (18) | 657 (26) | 662 (31) |
| Azure B | 613 | 649 (36) | 645 (32) | 654 (41) |
| Methylene green | 609 | 624 (15) | 626 (17) | 626 (17) |
| Buffer solution (pH 7.6) | | | | |
| Methylene blue | 665 | 681 (16) | 688 (23) | 698 (33) |
| Azure C | 620 | 638 (18) | 641 (21) | 651 (31) |
| Azure A | 633 | 652 (19) | 657 (24) | 671 (38) |
| 1,9-Dimethyl-phenothiazine | 592 | 666 (74) | 673 (81) | 683 (91) |
| Toluidine blue O | 632 | 650 (18) | 655 (23) | 666 (34) |
| Azure B | 613 | 633 (20) | 640 (27) | 648 (35) |
| Methylene green | 609 | 624 (15) | 624 (15) | 629 (20) |

Table 7 shows the light absorptions at 700 nm exhibited by the reaction liquids. In Table 7, the numerical values in parentheses show the differences between the light absorbance at 700 nm of the control and that of the example. As shown in Table 7, all phenothiazine-derivative colors had higher light absorbance at 700 nm in the presence of the respective shifting agents.

TABLE 7

| Phenothiazine-derivative color | Light absorbance at 700 nm (Abs.) | | | |
|---|---|---|---|---|
| | Control | Tartrazine | Yellow No. 5 | Red No. 5 |
| Buffer solution (pH 5.8) | | | | |
| Methylene blue | 0.097 (0) | 0.458 (0.368) | 0.523 (0.427) | 0.448 (0.352) |
| Azure C | 0.010 (0) | 0.021 (0.012) | 0.041 (0.032) | 0.055 (0.046) |
| Azure A | 0.025 (0) | 0.127 (0.102) | 0.180 (0.154) | 0.189 (0.163) |
| 1,9-Dimethyl-phenothiazine | 0.104 (0) | 0.335 (0.231) | 0.411 (0.307) | 0.540 (0.436) |
| Toluidine blue O | 0.023 (0) | 0.083 (0.060) | 0.122 (0.099) | 0.132 (0.109) |
| Azure B | 0.022 (0) | 0.090 (0.068) | 0.117 (0.095) | 0.115 (0.093) |
| Methylene green | 0.034 (0) | 0.130 (0.095) | 0.160 (0.125) | 0.152 (0.118) |
| Buffer solution (pH 7.6) | | | | |
| Methylene blue | 0.097 (0) | 0.484 (0.387) | 0.521 (0.424) | 0.448 (0.351) |
| Azure C | 0.007 (0) | 0.022 (0.015) | 0.040 (0.033) | 0.055 (0.048) |
| Azure A | 0.026 (0) | 0.135 (0.109) | 0.178 (0.152) | 0.197 (0.171) |
| 1,9-Dimethyl-phenothiazine | 0.115 (0) | 0.352 (0.236) | 0.420 (0.305) | 0.542 (0.427) |
| Toluidine blue O | 0.021 (0) | 0.085 (0.064) | 0.126 (0.106) | 0.147 (0.126) |
| Azure B | 0.020 (0) | 0.094 (0.074) | 0.116 (0.096) | 0.113 (0.093) |
| Methylene green | 0.034 (0) | 0.132 (0.097) | 0.153 (0.118) | 0.148 (0.114) |

Figure 3A:
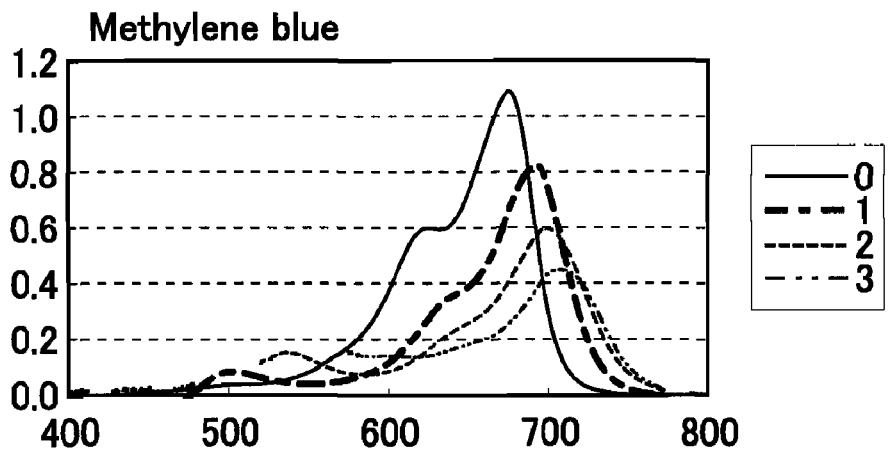
FIG. 3 shows graphs of the spectra of various phenothiazine-derivative colors in the presence of various color substances in Example 3 of the present invention, wherein A shows the result for methylene blue, B shows the result for Azure C, and C shows the result for Azure A (Fluka).
Figure 3B:
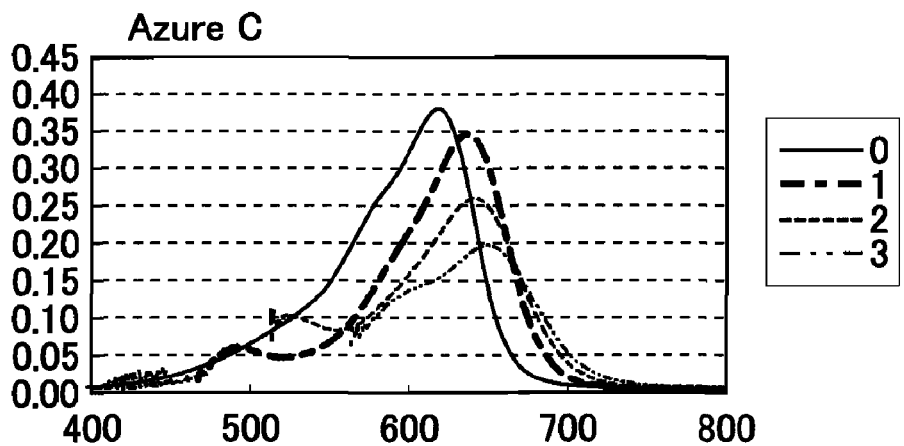
Figure 3C:
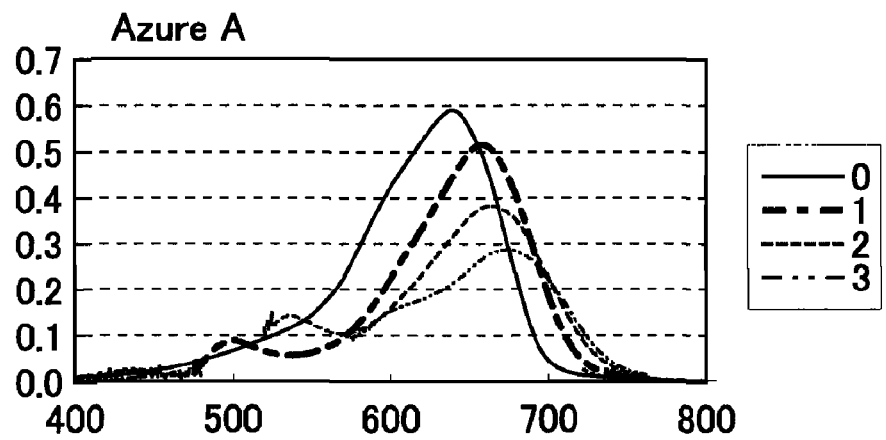
Figure 4D:
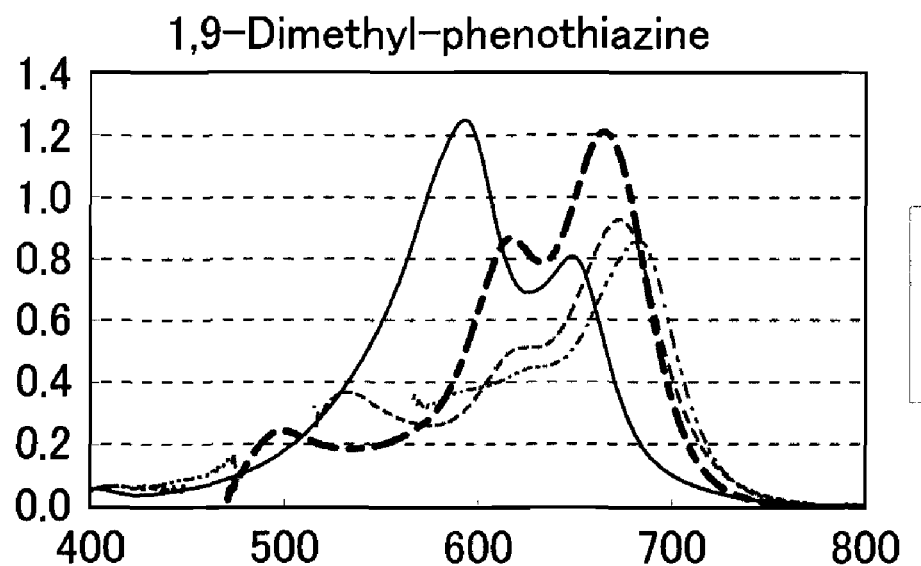
FIG. 4 shows graphs of the spectra of various phenothiazine-derivative colors in the presence of various color substances in Example 3 of the present invention, wherein D shows the result for 1,9-dimethyl-phenothiazine, and E shows the result for toluidine blue O.
Figure 4E:
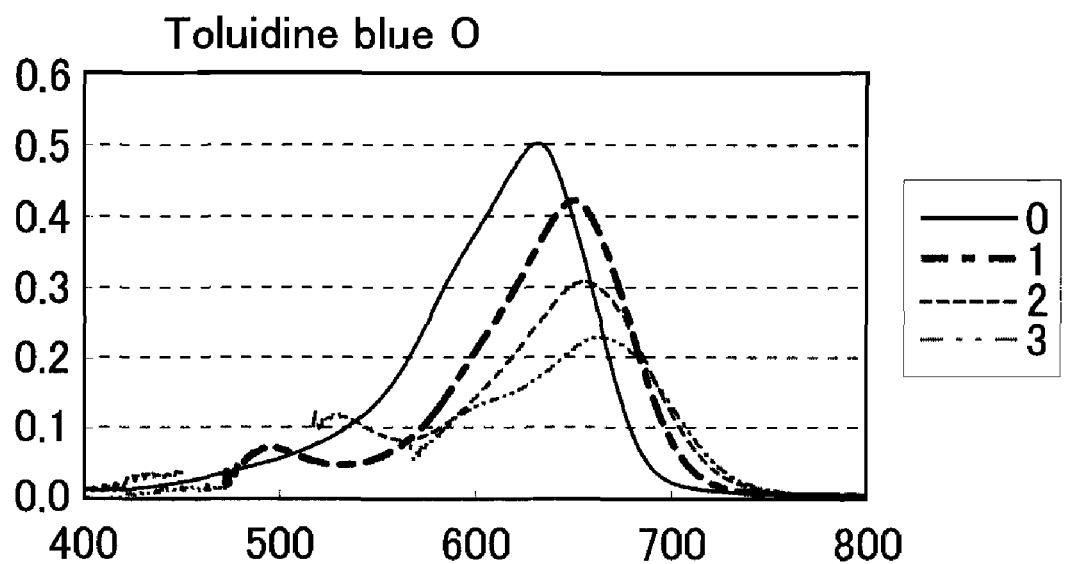
Figure 5F:
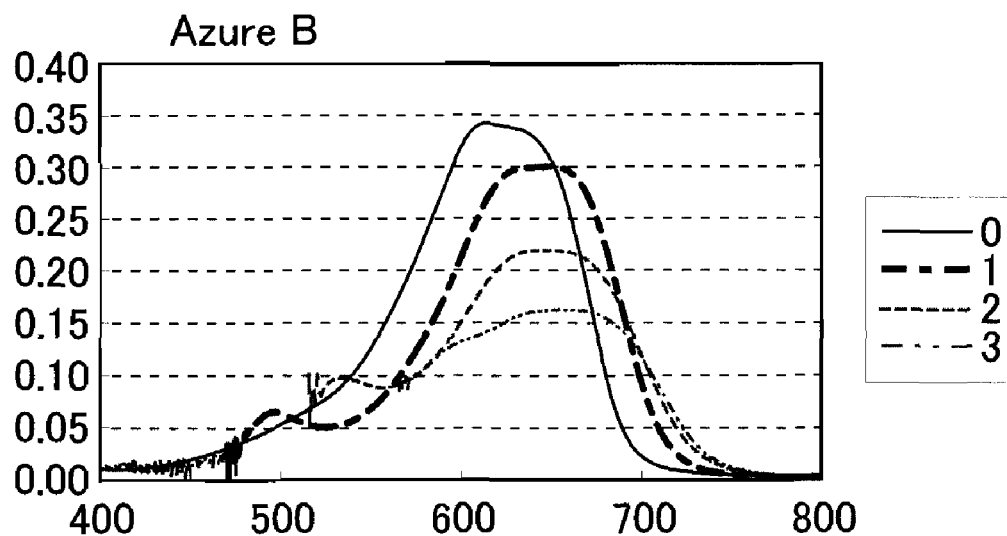
FIG. 5 shows graphs of the spectra of various phenothiazine-derivative colors in the presence of various color substances in Example 3 of the present invention, wherein F shows the result for Azure B, and G shows the result for methylene green.
Figure 5G:
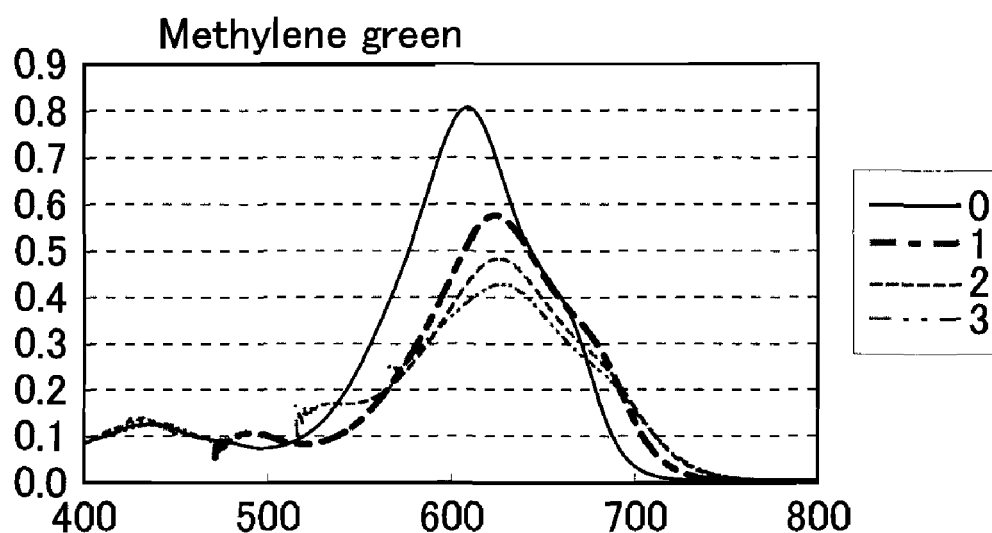

FIGS. 3 to 5 show the spectra of the reaction liquids containing various phenothiazine-derivative colors and various shifting agents. Here, these results are the spectra after deletion of the absorption spectra of the shifting agents. In FIGS. 3 to 5, A shows the results for methylene blue, B shows the results for Azure C, C shows the results for Azure A (Fluka), D shows the results for 1,9-dimethyl-phenothiazine, E shows the results for toluidine blue O, F shows the results for Azure B, and G shows the results for methylene green. Furthermore, in FIGS. 3 to 5, the solid line 0 shows the results for the control (to which no shifting agent was added), the broken line No. 1 shows the results for tartrazine, the broken line No. 2 shows the results for Food Yellow No. 5, and the broken line No. 3 shows the results for Food Red No. 2. In FIGS. 3 to 5, it was confirmed in all phenothiazine-derivative colors that the absorption spectrum was shifted toward the long-wavelength side in the presence of the shifting agent, compared with that of the control (the solid line 1).

EXAMPLE 4

A methylene blue-producing color-developer that easily decomposes, typically due to light, was brought together with a color substance (the shifting agent), and the effect of the color substance suppressing an increase in the background noise due to naturally occurring methylene blue was confirmed.

The second reagent (R2) that was the same as in Example 2 was prepared and then stored in a refrigerator for 30 days with the second reagent exposed to light. Here, the color substances added to the second reagent were No. 1 (tartrazine, 100 mg/L) and No. 3 (food additive Food Yellow No. 4, 100 mg/L) as in Example 2.

First, 78 µL of the first reagent (R1-3) described below and 13 µL of purified water were mixed and incubated at 37° C. for 5 minutes, and then 19.5 µL of the second reagent (R2) after storage was added. Then, a light absorbance ($A_0'$) at a wavelength of 694 nm in the reaction liquid immediately before adding the second reagent and a light absorbance ($A_5'$) at a wavelength of 694 nm in the reaction liquid at 5 minutes after adding the second reagent were measured using an automatic biochemical analyzing apparatus (product name JCA-BM8: manufactured by JEOL Ltd.), and the difference ($A_5'$-$A_0'$) was obtained. Furthermore, as in Comparative Example 3, the second reagent to which no color substance was added was used, and the same measurement was performed. Here, in order to compare the increases in the background of the second reagent equitably, a large amount of tartrazine was added to the first reagent (R1-3).

TABLE 8

| (First Reagent: R1-3) | |
|---|---|
| FPOX-CE (manufactured by Kikkoman Corporation) | 1.3 KU/L |
| POD | 5 KU/L |
| PIPES | 30 mmol/L (pH 7) |
| EMULGEN A-500 (manufactured by Kao Corporation) | 0.05 g/L |
| n-Dodecyl-αβ-D-maltoside | 2.5 g/L |
| Tartrazine | 1 g/L |

TABLE 9

|  | Com. Ex. 3 | Ex. 3 | |
| --- | --- | --- | --- |
|  | Color substance (—) | Color substance No. 1 | Color substance No. 3 |
| 694 nm ($A_5'-A_0'$) | 0.159 | 0.125 | 0.129 |

As shown in Table 9, in Example 4 using the second reagent to which the color substance was added, an increase in the light absorbance at 694 nm (an increase in the background) was suppressed compared with that of Comparative Example 3 using the second reagent to which no color substance was added. That is to say, although the color-developer easily decomposes due to light, when the color substance was added to the second reagent, light was blocked, and the natural occurrence of methylene blue was suppressed. Thus, when the color-developer and the color substance were put together, measurement in a long-wavelength range can be performed as described above. Moreover, for example, storage in a liquid form until use is also possible, and a reagent that is very useful in a measuring method using a color-developer that is susceptible to light is obtained.

EXAMPLE 5

A methylene blue-producing color-developer DA-67 that produces methylene blue through oxidation was irradiated with light in the presence of the color substance, and the effect of the color substance (the shifting agent) suppressing the decomposition of the color-developer (suppressing naturally occurring methylene blue) was confirmed.
(DA-67 Solution)
DA-67 as described in Example 2 was dissolved in 30 mmol/mL of MOPS-NaOH (pH 7.6) at a ratio of 0.05 mmol/mL.
(Color Substance Solutions)
The following color substances were dissolved in purified water at a ratio of 10 mmol/mL.

| No. 1 | Tartrazine |
| --- | --- |
| No. 2 | Food additive, Food Yellow No. 5 |
| No. 3 | Food additive, Food Red No. 2 |

Samples (10 mL each) were prepared by mixing the DA-67 solution, a color substance, and purified water so that the final concentration of DA-67 was 0.025 mmol/mL and the final concentration of color substance was a predetermined concentration (0.1 mmol/mL, 0.2 mmol/mL, or 0.4 mmol/mL). Transparent glass containers containing these samples were allowed to stand near a frosted window facing south and exposed to sunlight for 1 hour from 15:00 to 16:00. The temperature was 25° C. After exposure, the spectra were measured using a spectrophotometer (V-550, JASCO Corporation). Furthermore, as a control, purified water was used instead of the color substance solution, and the same measurement was performed. Table 10 shows the results obtained by measuring the light absorbance at the maximum absorption wavelength corresponding to each color substance of each sample. The maximum absorption wavelength of No. 1 (tartrazine) was 666 nm, that of No. 2 (Yellow No. 5) was 681 nm, and that of No. 3 (Red No. 2) was 646 nm. Here, in Table 10, "maximum color development light absorbance" refers to the light absorbance when methylene blue is produced from all DA-67 contained in each sample formulation, and "ratio of methylene blue produced" refers to the ratio of methylene blue produced after exposure, and shown as a ratio of light absorbance after exposure when the maximum color development light absorbance is taken as 100%.

TABLE 10

| Sample | Color substance Type (No.) | Color substance Final concentration (mmol/mL) | Light absorbance (Abs.) Before exposure | Light absorbance (Abs.) After exposure | Maximum color development light absorbance | Ratio of methylene blue produced (%) |
| --- | --- | --- | --- | --- | --- | --- |
| Control | — | — | 0.008 | 0.190 | 0.740 | 25 |
| 5-1 | 1 | 0.1 | 0.012 | 0.051 | 0.565 | 7 |
|  | 1 | 0.2 | 0.009 | 0.049 | 0.565 | 7 |
|  | 1 | 0.4 | 0.009 | 0.045 | 0.565 | 6 |
| 5-2 | 2 | 0.1 | 0.006 | 0.029 | 0.410 | 6 |
|  | 2 | 0.2 | 0.006 | 0.025 | 0.410 | 4 |
| 5-3 | 3 | 0.1 | 0.006 | 0.006 | 0.309 | 0 |
|  | 3 | 0.2 | 0.002 | 0.006 | 0.309 | 1 |
| 5-4 | 4 | 0.4 | 0.009 | 0.006 | 0.309 | −1 |

As shown in Table 10, in the case where DA-67 was exposed to sunlight in the presence of a color substance, an increase in the light absorbance due to the exposure was suppressed compared with that of the control to which no color substance was added. That is to say, the color substance suppressed the production (natural occurrence) of methylene blue from DA-67.

INDUSTRIAL APPLICABILITY

As described above, according to the present invention, for example, when the color substance is added to a reaction system containing a phenothiazine-derivative color, the phenothiazine-derivative color can be detected even at a wavelength longer than the wavelength that exhibits maximum absorption. Thus, for example, even in the case where a sample contains components that exhibit an absorption at 660 nm other than a target, the influence thereof can be averted in the detection of a phenothiazine-derivative color. Furthermore, since the absorption at 700 nm increases, for example, even an apparatus in which the detection wavelength is set to 700 nm can detect a phenothiazine-derivative color. In this manner, according to the method of the present invention, the conditions for detecting a phenothiazine-derivative color are improved, and, thus, the application range of a color-developer that produces a phenothiazine-derivative color and a phenothiazine-derivative color as a color-developer can be further increased compared with that of conventional examples.

The invention claimed is:
1. A method for detecting a phenothiazine-derivative color in a reaction system by measuring a light absorbance, comprising a step of detecting a phenothiazine-derivative color, wherein, in the detecting step, a phenothiazine-derivative color is detected in the presence of at least one color substance selected from the group consisting of a compound represented by Formula (K) below, a compound represented by Formula (II) below, and a flavonoid-based color:

$$R^1-N=N-R^2 \rightarrow \quad (I)$$

(in Formula (I),
R$^1$ is

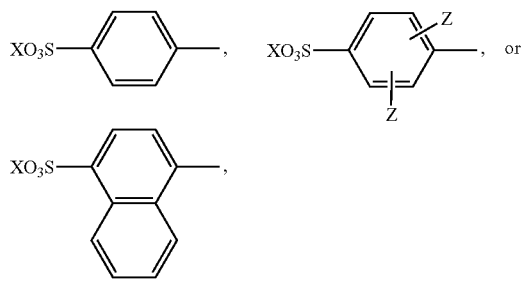

R$^2$ is and

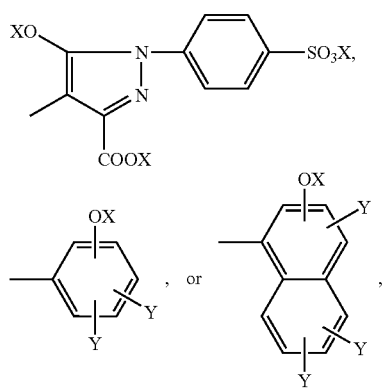

in R$^1$ and R$^2$,
X is hydrogen, a halogen, sodium or potassium,
Y is hydrogen or SO$_3$X,
Xs may be the same or different, and Ys may be the same or different, and
Z is hydrogen, a methyl group, or a methoxy group, and Zs may be the same or different); and

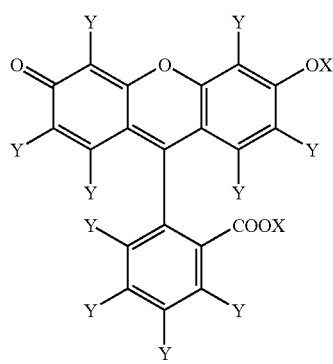

(II)

(in Formula (II),
X is hydrogen, a halogen, sodium, or potassium, and Xs may be the same or different, and
Y is hydrogen, a halogen, sodium or potassium, and Ys may be the same or different) wherein the measuring a light absorbance in the detecting step is the long wavelength side compared with the maxiumu absorption wavelength from 590 to 670 nm; and
wherein the method comprises a color-developer-adding step of
adding a color-developer that produces a phenothiazine-derivative color through oxidation-reduction to the reaction system, and
producing a phenothiazine-derivative color through oxidation-reduction between the color-developer and an oxidizing substance or reducing substance in the reaction system, wherein, in the step of detecting a phenothiazine-derivative color, a presence/absence or an amount of phenothiazine-derivative color produced is measured by measuring a light absorbance.

2. The detection method according to claim 1, wherein the compound represented by Formula (I) is at least one color substance selected from the group consisting of:
5-hydroxy-1-(4-sulfophenyl)-4-(4-sulfophenylazo)pyrazole-3-carboxylic acid and a salt thereof;
6-hydroxy-5-(4-sulfophenylazo)-2-naphthalenesulfonic acid and a salt thereof;
3-hydroxy-4-(4-sulfonaphthylazo)-2,7-naphthalenedisulfonic acid and a salt thereof;
6-hydroxy-5-[(2-methoxy-5-methyl-4-sulfonatophenyl)diazenyl]naphthalene-2-sulfuric acid and a salt thereof; and
7-hydroxy-8-(4-sulfonaphthylazo)-1,3-naphthalenedisulfonic acid and a salt thereof.

3. The detection method according to claim 1, wherein the compound represented by Formula (II) is at least one color substance selected from the group consisting of:
3',6'-dihydroxy-2',4',5',7'-tetraiodospiro[isobenzofuran-1(3H),9'-(9H) xanthene]-3-one and a salt thereof;
3',6'-dihydroxy-2',4',5',7'-tetrabromo-4,5,6,7,-tetrachlorospiro[isobenzofuran-1(3H),9'-[9H]xanthene]-3-one and a salt thereof;
4,5,6,7-tetrachloro-3',6'-dihydroxy-2',4',5',7'-tetraiodospiro[isobenzofuran-1(3H),9'-[9H]xanthene]-3-one and a salt thereof;
2,4,5,7-tetrabromo-3,6-dihydroxyxanthene-9-spiro-1'-3H-isobenzofuran-3'-one and a salt thereof; and
3,6-dihydroxyxanthene-9-spiro-1'-3'H-isobenzofuran-3'-one and a salt thereof.

4. The detection method according to claim 1, wherein a ratio of the color substance added to the reaction system is 1 to 1000 mol per 1 mol of phenothiazine-derivative color.

5. The detection method according to claim 1, wherein the wavelength for measuring a light absorbance in the detecting step is 610 to 730 nm.

6. The detection method according to claim 1, wherein the color substance is added to the reaction system before the detecting step.

7. The detection method according to claim 1, wherein the phenothiazine-derivative color is diaminophenothiazine or a derivative thereof.

8. The detection method according to claim 1, wherein the phenothiazine-derivative color is a compound represented by Formula (III) below, a tautomer or stereoisomer thereof, or a salt thereof:

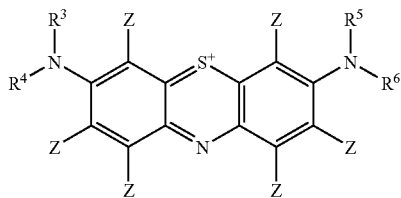

(in Formula (III),
$R^3$ to $R^6$ are each a hydrogen atom or an alkyl group, and may be the same or different, and each Z is a hydrogen atom, an alkyl group, a nitro group, an amino group, a halogen, a sulfo group, or a carboxyl group, and may be the same or different).

9. The detection method according to claim 8, wherein, in $R^3$ to $R^6$, the alkyl group is a linear or branched alkyl group having 1 to 6 carbon atoms.

10. The detection method according to claim 8, wherein, in $R^3$ to $R^6$, the alkyl group is a methyl group.

11. The detection method according to claim 8, wherein, in Z, the alkyl group is a linear or branched alkyl group having 1 to 6 carbon atoms.

12. The detection method according to claim 8, wherein, in Z, the alkyl group is a methyl group.

13. The detection method according to claim 1, wherein the phenothiazine-derivative color is at least one selected from the group consisting of methylene blue, azure A, azure B, azure C, toluidine blue O, 1,9-dimethyl-3,7-bis(dimethylamino)phenothiazine salt, and methylene green.

14. The detection method according to claim 1, wherein the phenothiazine-derivative color is methylene blue.

15. The detection method according to claim 1, wherein the phenothiazine-derivative color is methylene blue, and the color-developer is at least one selected from the group consisting of 10-(carboxymethylaminocarbonyl)-3,7-bis(dimethylamino)phenothiazine and a salt thereof, and leucomethylene blue.

16. The detection method according to claim 1, comprising a step of adding a phenothiazine-derivative color as a color-developer to the reaction system, and causing oxidation-reduction between the phenothiazine-derivative color and a reducing substance in the reaction system, wherein, in the step of detecting a phenothiazine-derivative color, a presence/absence or an amount of decrease in the phenothiazine-derivative color added to the reaction system is measured by measuring a light absorbance.

17. The detection method according to claim 16, wherein the phenothiazine-derivative color is methylene blue, and leucomethylene blue is produced from methylene blue through oxidation-reduction between the methylene blue and a reducing substance in the reaction system.

18. The detection method according to claim 1, wherein a ratio of the color substance in the reaction system is 0.1 to 1000 mol per 1 mol of color-developer.

19. The detection method according to claim 1, wherein a final concentration of the color substance in the reaction system is $10^{-6}$ to 0.1 mol/L.

20. A method for measuring a target component in a sample by detecting a phenothiazine-derivative color, comprising:
(A) a step of producing an oxidizing substance or reducing substance from the target component in the sample;
(B) a color-developer-adding step of adding, to the sample, a color-developer that produces a phenothiazine-derivative color through oxidation-reduction;
(C) a step of producing a phenothiazine-derivative color through oxidation-reduction between the oxidizing substance or reducing substance and the color-developer;
(D) a step of detecting a phenothiazine-derivative color using the method for detecting a phenothiazine-derivative color according to claim 1, and measuring a presence/absence or an amount of the phenothiazine-derivative color produced; and
(E) a step of determining a presence/absence or an amount of the target component in the sample based on a result of the measurement.

21. A method for measuring a target component in a sample by detecting a phenothiazine-derivative color, comprising:
(A) a step of producing an oxidizing substance or reducing substance from the target component in the sample;
(B') a step of adding a phenothiazine-derivative color as a color-developer to the sample;
(C') a step of causing oxidation-reduction between a reducing substance produced by the target component in the sample and the phenothiazine-derivative color;
(D') a step of detecting a phenothiazine-derivative color using the method for detecting a phenothiazine-derivative color according to claim 1, and measuring a presence/absence or an amount of decrease in the added phenothiazine-derivative color; and
(E) a step of determining a presence/absence or an amount of the target component in the sample based on a result of the measurement.

22. The measuring method according to claim 20, wherein the target component is glycated protein.

23. The measuring method according to claim 20, wherein, in the step (A), hydrogen peroxide is produced as an oxidizing substance by causing fructosyl amino acid oxidase to act on glycated protein.

24. The measuring method according to claim 20, wherein, in the step (C), a phenothiazine-derivative color is produced by causing oxidation-reduction between the hydrogen peroxide and the color-developer using an oxidizing enzyme.

25. The measuring method according to claim 20, wherein the phenothiazine-derivative color is methylene blue, and the color-developer in the step (B) is at least one of 10-(carboxymethylaminocarbonyl)-3,7-bis(dimethylamino)phenothiazine and a salt thereof.

* * * * *